(12) United States Patent
Pavlidis et al.

(10) Patent No.: US 7,138,905 B2
(45) Date of Patent: Nov. 21, 2006

(54) CONTROLLED ENVIRONMENT THERMAL IMAGE DETECTION SYSTEM AND METHODS REGARDING SAME

(75) Inventors: Ioannis Pavlidis, Houston, TX (US); Michael E. Bazakos, Bloomington, MN (US); Vassilios Morellas, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 192 days.

(21) Appl. No.: 10/991,595

(22) Filed: Nov. 18, 2004

(65) Prior Publication Data

US 2006/0116555 A1    Jun. 1, 2006

(51) Int. Cl.
    G07D 7/00    (2006.01)
(52) U.S. Cl. .................. 340/5.81; 340/5.82; 340/5.83; 382/115; 382/118
(58) Field of Classification Search ............. 340/5.81, 340/5.82, 5.83, 5.53; 600/504; 374/45; 382/100, 115, 116, 118, 224
    See application file for complete search history.

(56) References Cited

U.S. PATENT DOCUMENTS

| | | | |
|---|---|---|---|
| 2,944,542 A | 7/1960 | Barnett et al. |
| 3,847,142 A | 11/1974 | Williams, Jr. et al. |
| 4,403,615 A | 9/1983 | Hoehner |
| 4,500,784 A | 2/1985 | Hacskaylo |
| 4,520,504 A | 5/1985 | Walker et al. |
| 4,878,116 A | 10/1989 | Thomas et al. |
| 4,940,059 A | 7/1990 | Voelz |
| 5,013,917 A | 5/1991 | Ulich |
| 5,099,852 A | 3/1992 | Meister et al. |
| 5,221,919 A | 6/1993 | Hermans |
| 5,287,183 A | 2/1994 | Thomas et al. |
| 5,339,817 A | 8/1994 | Nilsson |
| 5,361,769 A | 11/1994 | Nilsson |
| 5,363,311 A | 11/1994 | Garbo |
| 5,370,121 A | 12/1994 | Reichenberger et al. |
| 5,406,956 A | 4/1995 | Farwell |
| 5,507,291 A | 4/1996 | Stirbl et al. |
| 5,603,328 A | 2/1997 | Zucker et al. |
| 5,689,241 A | 11/1997 | Clarke, Sr. et al. |
| 5,703,367 A | 12/1997 | Hashimoto et al. |
| 5,771,261 A | 6/1998 | Anbar |
| 5,774,571 A | 6/1998 | Marshall |
| 5,860,922 A | 1/1999 | Gordon et al. |
| 5,860,935 A | 1/1999 | Blaszynski et al. |

(Continued)

FOREIGN PATENT DOCUMENTS

EP    0867830 A2    9/1998

(Continued)

OTHER PUBLICATIONS

U.S. Appl. No. 09/776,470, filed Feb. 2, 2001, Pavlidis et al.

(Continued)

*Primary Examiner*—Davetta W. Goins
(74) *Attorney, Agent, or Firm*—Kris T. Fredrick

(57) ABSTRACT

Thermal infrared image data of at least a region of a face of a person in an enclosure is provided. The enclosure, for example, may include a first enclosed volume and a second enclosed volume physically separated from the first enclosed volume. The first enclosed volume may include an entrance door sized to allow a person to enter the first enclosed volume. The enclosure provides a controlled environment for performing measurements (e.g., capturing thermal infrared image data) for use in determining a physiological state of a person (e.g., anxiety, deception, etc.).

39 Claims, 12 Drawing Sheets

U.S. PATENT DOCUMENTS

| | | | |
|---|---|---|---|
| 5,876,334 | A | 3/1999 | Levy |
| 5,900,942 | A | 5/1999 | Spiering |
| 5,940,139 | A | 8/1999 | Smoot |
| 6,002,505 | A | 12/1999 | Kraenert et al. |
| 6,464,646 | B1 | 10/2002 | Shalom et al. |
| 6,757,412 | B1 | 6/2004 | Parsons et al. |
| 6,854,879 | B1 | 2/2005 | Pavlidis |
| 6,879,709 | B1 * | 4/2005 | Tian et al. .................. 382/118 |
| 2002/0062089 | A1 | 5/2002 | Johnson, Jr. |
| 2002/0091336 | A1 | 7/2002 | Cohen |
| 2002/0183627 | A1 | 12/2002 | Nishii et al. |
| 2003/0016726 | A1 | 1/2003 | Pavlidis |
| 2003/0120140 | A1 | 6/2003 | Bango |
| 2003/0204144 | A1 | 10/2003 | Lin |

FOREIGN PATENT DOCUMENTS

| | | |
|---|---|---|
| EP | 0867830 A3 | 9/1998 |
| EP | 0 885 587 A1 | 12/1998 |
| JP | 359195134 A | 11/1984 |
| WO | 9216910 A | 10/1992 |
| WO | 98/08431 | 3/1998 |
| WO | 9906974 A | 2/1999 |

OTHER PUBLICATIONS

Buddharaju et al., "Face Recognition in the Thermal Infrared Spectrum," Proceedings of the 2004 IEEE Computer Society Conference on Computer Vision and Pattern Recognition Workshops (CVPRW04), Washington, D.C. Jun. 27-Ju. 2, 2004, 8 pgs.

Fendt et al., "The neuroanatomical and neurochemical basis of conditioned fear," Neurosci Biobehav Rev, 23(5):743-60 (May, 1999).

Fujimasa et al., "Converting Far-Infrared Image Information to Other Physiological Data," IEEE Engineering in Medicine and Biology, vol. 19, No. 3, pp. 71-75, 2000.

Gyaourova et al., "Fusion of infrared and visible images for face recognition", Proccedings of the 8th European Conference on Computer Vision, Prague, Czech Republic, May 11-14, 2004, pp. 456-468.

Gose et al., "Pattern Recognition and Image Analysis," pp. 159-186, Prentice-Hall, Upper Saddle River, NJ (1993).

Holden, "Panel Seeks Truth in Lie Detector Debate," Science, vol. 291, No. 9, p. 967,2001.

Iwatani, "An Estimation Method of Skin Blood Flow Rate Using Heat Flow Analysis," Japanese Journal of Medical Electronics and Biological Engineering, vol. 20, No. 3, pp. 249-255, includes English Abstract, 1982.

Jacquez et al., "The spectral reflectance of human skin in the region 0.7-2.6 μm, " Technical Report, 189, Army Medical Research Laboratory, Fort Knox (Apr., 1955).

Jordan et al., "Hierarchical Mixtures of Experts and the EM Algorithm," Neural Computation, vol. 6, pps. 181-214 (1994).

Levine et al., "The energy expended in chewing gum," New England Journal of Medicine, 341(27):2100 (Dec. 1999).

Levine et al., "Face of Fear", The Lancet, vol. 357, No. 9270, Jun. 6, 2001.

Measuring Intelligence, www.bbc.co.uk/science/hottopics/intelligence/iq.shtml. Apr. 2002.

Mendez, The Master of Disguise, Wiliam Morrow and Co., New York, N.Y.; cover page, title page, copyright page and table of contents only; 4 pgs. (1999).

Moghaddam et al., "Probabilistic Visual Learning for Object Recognition," IEEE Trans. Pattern Analysis and Machine Intelligence, 19(7):696-710 (Jul., 1997).

Otsu, "A Threshold Selection Method from Gray-Level Histograms," IEEE Transactions on Systems, Man & Cybernetics, vol. 9, No. 1, pps. 62-65 (1979).

Pavlidis et al., "Automatic Detection of Vehicle Occupants-The Imaging Problem and Its Solution, " Machine Vision and Applications, vol. 11, No. 6, pp. 313-320, 2000.

Pavlidis et al., "Monitoring of Periorbital Blood Flow Rate Through Thermal Image Analysis and its Application to Polygraph Testing", Proceedings 23rd Annual International Conference of the IEEE Engineering in Medicine and Biology Society, Instanbul, Turkey, Oct. 25-28, 2001.

Pavlidis et al., "Automatic passenger counting in the high occupancy vehicle (HOV) lanes" Proceedings 1999 Annual Meeting of the Intelligent Transportation Society of America, Washington, D.C. (Apr. 19-22, 1999).

Pavlidis et al., "A near-infrared fusion scheme for automatic detection of vehicle passengers," Proceedings 1999 IEEE Workshop on Computer Vision Beyond the Visible Spectrum: Methods and Applications, 41-48, Fort Collins, C.O. (Jun. 22, 1999).

Pavlidis et al., "Thermal Imaging for Anxiety Detection," 2000 IEEE Workshop on Computer Vision Beyond the Visible Spectrum: Methods and Applications, pp. 104-109, Hilton Head Island, South Carolina, Jun. 16, 2000.

Pavlidis et al., "The Imaging Issue in an Automatic Face/Disguise Detection System," 2000 IEEE Workshop on Computer Vision Beyond the Visible Spectrum: Methods and Applications, pp. 15-24, Hilton Head Island, South Carolina, Jun. 16, 2000.

Pavlidis, et al., "Thermal Image Analysis for Polygraph Testing," IEEE Engineering in Medicine and Biology Magazine, 21(6) pp. 56-64, Nov. 2002.

Pavlidis et al., "Seeing through the face of deception," Nature, 415:35, Jan. 3, 2002.

Pavlidis et al., "Lie detection using thermal imaging," Thermosense, Proceedings of SPIE, vol. 5405, pp. 270-279, Orlando, Florida, Apr. 13-15, 2004.

Penev et al., "Local feature analysis: a general statistical theory for object representation," Network: Computation in Neural Systems, 7(3):477-500 (Aug., 1996).

Pèntland et al., "Face Recogniton for smart environment," IEEE Computer, 33(2):50-55 (Feb., 2000).

Phillips et al., "The FERET database and evaluation procedure for face-recogniton algorithms," Image and Vision Computing, 16(5):295-306 (Apr., 1998).

Prokoski "Disguise detection and identification using infrared imagery," Proceedings of SPIE, Optics, and Images in Law Enforcement II, 339:37-31, A.S. Hecht, ed., Arlington, V.A. (May, 1982).

Sabins, Remote Sensing, Principles and Interpretation, W.H. Freeman and Company, New York, N.Y.; cover page, title page, copyright page and table of contents only; 7 pgs. (1997, 3rd ed.).

Singh et al., Infrared and Visible Image Fusion for Face Recognition, Proceedings of the SPIE Defense and Security Symposium, Orlando, Florida, Apr. 12-16, 2004, vol. 5404, pp. 585-596.

Sliney, "Laser and LED eye hazards: safety standards," Optics and Photonics News, pp 32- (Sep. 1997).

Visionics Corporation, "Face detection constantly searches for faces in a datastream" Jersey City, N.J.; retrieved from the Internet on Jun. 25, 2001, <URL:http://www.visionics.com/faceit/tech/detect.html>, 1 pg.

Wiskott et al., "Face recognition by elastic bunch graph matching," IEEE Trans. Pattern Analysis and Machine Intelligence, 19(7):775-779 (Jul., 1997).

Zhu et al., "Region Competition: Unifying Snakes, Region Growing, and Bayes/MDL for Multiband Image Segmentation," IEEE Transactions on Image Analysis and Machine Intelligence, vol. 18, No. 9 (1996) pp. 884-900.

\* cited by examiner

CONTROLLED ENVIRONMENT THERMAL IMAGE DETECTION SYSTEM AND METHODS REGARDING SAME

BACKGROUND OF THE INVENTION

The present invention relates generally to thermal analysis systems and methods. More particularly, the present invention pertains to use of such systems and methods in a controlled environment (e.g., use of thermal analysis in the detection of physiological response characteristics representative of one or more altered human states such as anxiety, alertness, fear, depression, etc., or use of thermal analysis to detect deception, such as like a polygraph).

In many situations, detection of one or more characteristics or behaviours of an individual is very important. For example, in various high-end security applications, e.g., at an embassy building where there is a need to know who certain individuals are within a particular setting and/or what individuals are about to do within a particular setting, detection of one or more characteristics of an individual is required. Further, for example, such detection systems and methods may not only be required in high-end security situations, but may also be needed in other settings such as various government buildings, schools, airports, and border control points. As such, systems for detection of, for example, deception or anxiety associated with individuals need to be developed and implemented.

Generally, certain recent biometric technologies (e.g., such as face recognition systems that may be able to match prestored data regarding a particular individual to real time collected data of an individual) have been developed which may be used in situations such as those described above. However, such systems have problems when employed in a realistic setting. For example, many face recognition systems are only applicable to repeat offenders with archived facial pictures. As such, these systems cannot address the case of a person in a security setting who has a clear record, or no record, that appears for the first time in a critical facility or any other civilian facility (e.g., an airport), and who may be, for example, attempting to do either harm or smuggle harmful materials. For example, a foreign national may not be captured when trying to smuggle explosives into the country as the foreign national may not have a record. However, an immigration officer with an experienced eye can detect an anxious state of such an individual who has no record and initiate an examination of the individual and the individual's belongings. Generally, deception when answering questions, alertness, anxiety, and even fear, accompany such people who are involved in terrorist or harmful activities at the time of their action. Manners to detect such characteristics and/or individuals with such characteristics are needed.

Traditional human identification systems used in circumstances such as those described above generally seek to detect an answer to the question, "Who are you?" Thereafter, upon determining who the person is, the potential of such an individual's risk is then based on the identification of the person. However, as described above, the identification of such persons may not be possible or may at least be problematic, e.g., the problematic identification of a person with no record. As such, when persons cannot be effectively identified, the risk posed by such an individual cannot be determined.

The use of interrogation of an individual by certain personnel, e.g., security agents, to detect potentially dangerous individuals has been conventionally used. However, it is unrealistic to expect ticket or security agents, for example, in a border or airport setting, to perform subject questioning of the same quality as a professional psychologist in order to detect, for example, deception on the part of an individual, or, for example, to detect anxiety in an individual. Likewise, it would be extremely costly to employ highly skilled psychologists at a massive scale to perform such duties. Even if such personnel could be hired, there would be an inescapable variability to such questioning and almost impossible to establish a baseline for who may pose a danger in such settings, e.g., based on anxiety or deception.

Polygraph testing is one standard security procedure used by various entities, e.g., governmental bodies, the military, etc., to detect deception in an individual. The objective of polygraph testing is to ascertain if the subject under investigation truthfully or deceitfully answers the questions presented thereto. Specially trained psychologists structure the questions to maximize elicitation.

Generally, during the testing, three physiological parameters are closely monitored. Such physiological parameters include blood flow rate, breathing rate, and perspiration rate. Typically, such physiological parameters are recorded using invasive methods and produce scalar values over time, e.g., signals. Then, a scoring system is used to quantify the subject's response and classify the subject's response as deceitful or truthful, i.e., deceptive or non-deceptive.

However, the success rate for conventional polygraph testing varies depending on the circumstances and persons being questioned. In some circumstances, the success rate may be very high, while in others, the success rate may be much lower.

There is generally a need for improved detection systems such as those that may become necessary to detect deception of an individual or anxiety of an individual at airports, borders, government buildings, etc.

SUMMARY OF THE INVENTION

According to the present invention, thermal image analysis methods and systems are provided in a controlled environment such that, for example, an individual's privacy is maintained and/or measurements used to make characteristic determinations are not contaminated (e.g., a controlled environment within an enclosure, for example, with reduced noise from a surrounding environment that may distract individuals, with controlled lighting and temperature that may affect the individual or the equipment being used, etc.). To provide such a controlled environment, an enclosure or booth is provided in which an individual may enter. Thermal image analysis may then be conducted in the booth to provide a determination that the individual is exhibiting higher than usual anxiety or is being deceitful in response to questions posed thereto.

In one or more embodiments according to the present invention, a method for use in detecting a physiological state of a person is described. The method may include one or more of the following features or steps: providing an enclosure that includes a first enclosed volume and a second enclosed volume physically separated from the first enclosed volume; an enclosure that includes an entrance door sized to allow a person to enter the first enclosed volume; controlling one or more characteristics of the environment (e.g., temperature, light intensity, noise, etc.) within the first enclosed volume of an enclosure; permitting only a single person to enter the first enclosed volume through an entrance door; asking a person within the first enclosed volume one or more questions so as to elicit a response from the person; providing thermal infrared image data of at least a region of the face of a person during at least a portion of the response from the person using at least one thermal infrared imaging device (e.g., the thermal infrared image data to determine a physiological state of a person such as anxiety or deception); and a thermal infrared imaging device positioned within a second enclosed volume of the enclosure.

Further, in one or more other embodiments according to the present invention, the method may include one or more of the following features or steps: an exit door of the enclosure sized to allow a person to exit the first enclosed volume (e.g., the entrance door and the exit door provide different openings of the enclosure); permitting the person within the first enclosed volume to exit the enclosure via the exit door; a plurality of enclosures positioned side by side; an enclosure or a plurality of enclosures that are portable; moving one or more of the enclosures from a first location to a second location; allowing a person to be seated at a position within the first enclosed volume; controlling at least one characteristic selected from a group of temperature, light intensity, air movement, and noise; and sensing one or more environmental parameters within the first enclosed volume and controlling one or more of the characteristics of the environment within the first enclosed volume based thereon.

Yet further, in one or more other embodiments according to the present invention, the method may include one or more of the following features or steps: prerecording one or more questions and presenting the one or more prerecorded questions to the person in the enclosure; displaying an animated or a video recorded figure presenting the one or more prerecorded questions to the person; detecting one or more responses from the person and synchronizing the presentation of the one or more prerecorded questions with the one or more detected responses from the person; permitting a person to enter the first enclosed volume through the entrance door through an authorization process that permits the entrance door to be unlocked; focusing a thermal infrared image device operable to provide thermal image data on at least the region of the face of the person and capturing thermal image data from at least a region of the face of the person during at least a portion of the response from the person; providing thermal image data from at least a region of the face of the person and transforming the thermal image data to blood flow rate data for use in determining whether the person is deceptive or non-deceptive (e.g., classifying the person as deceptive or non-deceptive based on a change of blood flow rate over time in the at least one region of the face); providing measurement of one or more physiological parameters in addition to the thermal image data and using thermal infrared image data and the one or more physiological parameters to determine a physiological state of a person; and providing thermal infrared image data to a computing apparatus with the computing apparatus positioned within the second enclosed volume.

In one or more embodiments according to the present invention, a system for use in detecting a physiological state of a person is described. The system may include one or more of the following features: an enclosure sized to accommodate only a single person therein, wherein the enclosure comprises a first enclosed volume and a second enclosed volume physically separated from the first enclosed volume; an entrance door sized to allow a person to enter the first enclosed volume; one or more environment control devices for use in controlling one or more characteristics of the environment within the first enclosed volume; a display apparatus and a speaker apparatus operable to present one or more prerecorded questions to a person occupying the first enclosed volume so as to elicit one or more responses therefrom; a thermal infrared imaging device positioned within the second enclosed volume operable to provide thermal infrared image data of at least a region of the face of a person when the first enclosed volume is occupied by the person; and a computing apparatus operable upon the thermal infrared image data to determine a physiological state of the person (e.g., anxiety or deception) occupying the first enclosed volume.

Further, in one or more other embodiments according to the present invention, the system may include one or more of the following features: an exit door of the enclosure sized to allow a person to exit the first enclosed volume (e.g., the entrance door and the exit door may be different openings of the enclosure); a plurality of enclosures positioned side by side; one or more enclosures that are portable and movable from a first location to a second location (e.g., one or more enclosures that include a set of transfer wheels on a lower surface thereof); a seat positioned within the first enclosed volume of the enclosure to allow a person to be seated at a position therein; and one or more environment control devices such as an air modification apparatus operable to adjust temperature within the first enclosed volume, a light source operable to adjust light intensity within the first enclosed volume, an air modification apparatus operable to adjust air flow within the first enclosed volume, or any other environment control device for adjusting a characteristic of the environment.

Yet further, in one or more other embodiments according to the present invention, the system may include one or more of the following features: a display apparatus and a speaker apparatus that are operable under control of the computing apparatus to provide an animated or a video recorded figure presenting one or more prerecorded questions to the person; a microphone located in the first enclosed volume for use in detecting one or more responses from the person in the first enclosed volume and a display apparatus and a speaker apparatus are operable under control of the computing apparatus to synchronize the one or more prerecorded questions with the one or more detected responses from the person; an identification authorization apparatus associated with the entrance door to provide authorization to a person waiting to enter the first enclosed volume (e.g., the entrance door being unlocked only upon a person receiving such authorization); a computing apparatus operable to determine anxiety or deception in the person based on thermal infrared image data (e.g., computing apparatus that is operable to transform the thermal infrared image data to blood flow rate data such as, change in blood flow rate, for use in determining whether the person is deceptive or non-deceptive); apparatus for providing measurement of one or more physiological parameters in addition capturing the thermal infrared image data and a computing apparatus that is operable to determine whether the person is deceptive or non-deceptive using the thermal infrared image data and the one or more physiological parameters; and a computing apparatus that is positioned in the second enclosed volume.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE EMBODIMENTS

DETAILED DESCRIPTION OF THE EMBODIMENTS

Figure 1:
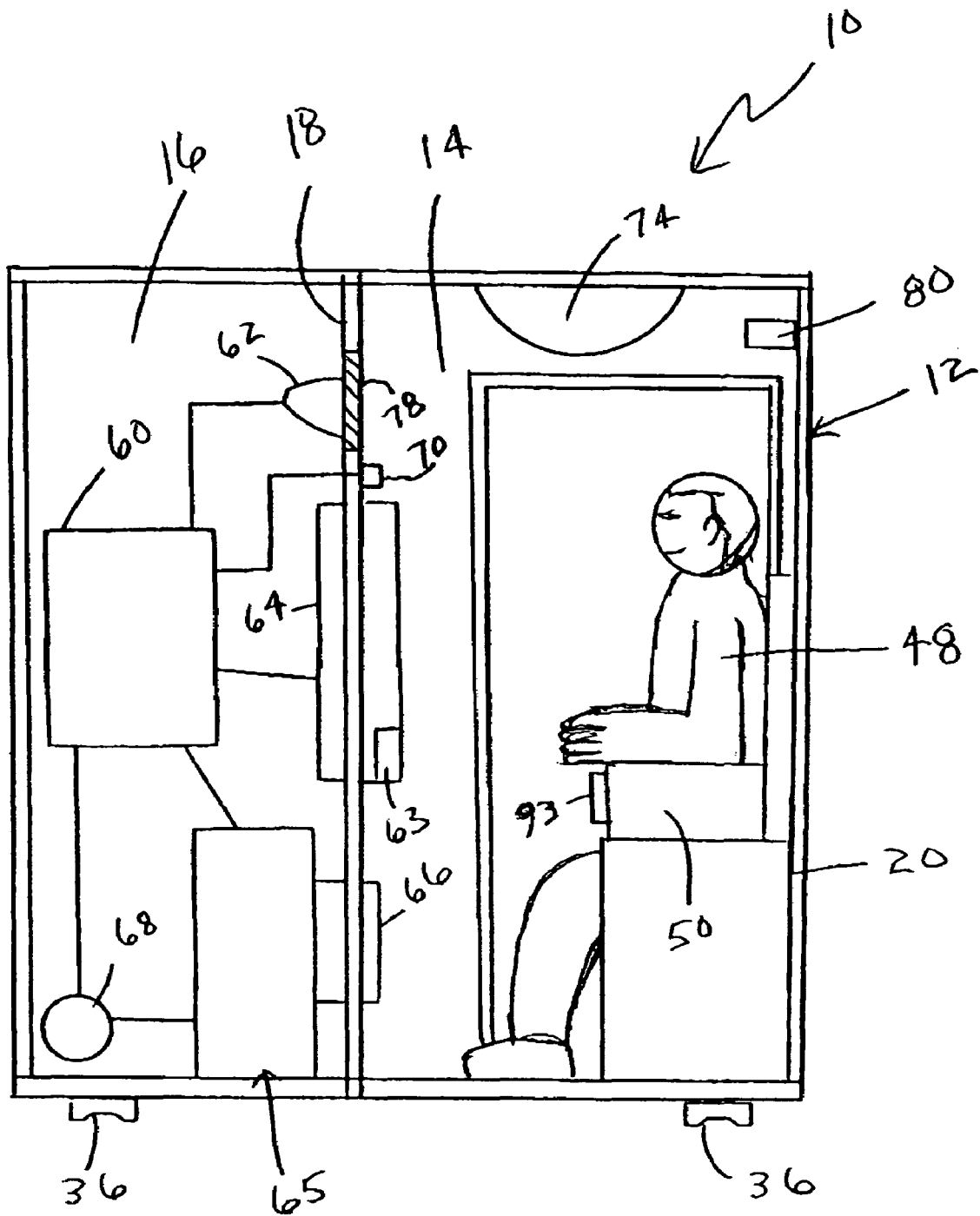
FIG. 1 is a general illustration of a detection system according to the present invention including an enclosure (e.g., booth) having an entrance wall thereof removed to view the interior of the enclosure.

One or more embodiments of the present invention shall be described generally with reference to FIGS. 1–5. Thereafter, additional embodiments of the present invention shall be described with further reference to FIGS. 6–16.

Generally, the present invention provides methods and systems for use in detecting a physiological state of a person through the analysis of thermal infrared image data. The thermal infrared image data for at least a region of the face of the person is captured in a controlled environment. The method and system described herein may be used to determine one or more different physiological states of a person. For example, depression, periods of dementia, anxiety, deception, etc., may be determined.

Further, generally, the present invention provides methods and systems that include acquisition of thermal infrared image data during at least a part of an interrogation session of the person (e.g., question and answer time periods) performed in a controlled environment. Such thermal infrared image data is then used to determine a physiological state of a person, for example, determining whether the person is deceptive or not deceptive with respect to the answers provided in the interrogation session, and/or whether the person is exhibiting anxiety during the interrogation.

For example, in one embodiment, facial thermal imagery using a mid-infrared camera may be performed. Thereafter, the raw thermal image data may be transformed to blood flow rate data through thermo-dynamic modeling. Finally, classifying a person as deceptive or non-deceptive may be performed based on one or more different classification processes (e.g., analysis of blood flow rate data, such as change in blood flow rate).

As used herein, and in interest of brevity, the term anxiety shall identify a set of feelings. This set of feelings includes alertness, anxiety, fear, and the like. Such a set of feelings are generally symptomatic in individuals at the time individuals are engaged in certain activities, such as terroristic or illegal activities. Such feelings or symptoms are produced by the sympathetic system and cannot be totally controlled by the person. As such, they provide a biometric indicator (e.g., measurable physiological response) that is extremely difficult to conceal. This biometric can provide valuable clues in many circumstances, such as, for example, to security personnel of critical facilities wherein potential suspects may be "immune" to identification biometrics (e.g., first time offenders, where no facial record is available). Systems and methods based on such a biometric can be used to prevent serious security issues, such as, for example, smuggling narcotics at border control points, terrorists at foreign facilities or at airports, etc. Such a system and method could be used to identify potential offenders allowing authoritative personnel to intervene on a selected basis.

Further, when reference is made to determining deception of a person, it is being determined whether a person is providing false responses to questions being presented thereto (e.g., the likelihood of such responses being false).

Irregardless of the process that determines a physiological state of a person using the thermal infrared image data (e.g., determination of anxiety or deception), the present invention provides a controlled environment in which such processes may be implemented such as shown by the generalized exemplary detection system 10 shown illustratively in FIG. 1. The controlled environment detection system 10, for example, at least in one embodiment, relies on monitoring, detecting, and measuring certain physiological changes due to a set of physiological stimuli. Such physiological changes are controlled by the sympathetic/parasympathetic system of the body of a person, and thus are outside of their own control.

The present invention, for example, addresses one or more challenges of measuring such physiological changes. For example, the present invention isolates the subject from the surroundings, thus protecting the privacy of the subject, making the subject feel more at ease, and at the same time providing a controlled environment for the operation of the detection system (e.g., reducing complexity of the detection system).

Further, for example, to reduce the variability of the psychological stimuli used to effect the certain physiological changes, a virtual agent is provided to conduct an interview with a person in a controlled environment. Such use of a virtual agent standardizes the interview process and solves the problem of employing a large number of highly skilled examiners in, for example, security checkpoints.

As used herein, when the term "virtual" is used to describe the interrogator, it means that the interrogator is not a human individual (e.g., the interrogator is a pre-recorded message or pre-recorded individual presenting such a message or questions).

Further, for example, to avoid subject intimidation, various components of the detection system (e.g., the infrared camera, equipment, etc.) are hidden from public view. Further, one or more of such components may also be hidden from view of the person being interrogated or interviewed.

Likewise, for example, to allow for effective and efficient use of the present invention, the enclosures (e.g., booths) provided herein are modular and portable (e.g., mobile). As such, the enclosures can be repositioned within, for example, a building very easily and effectively.

The detection system according to the present invention, at least in one embodiment, relies primarily on non-invasive technologies. A very short preparation time for the individual or person being interviewed is required (e.g., no polygraph leads need be attached to the individual). For example, capture of data and analysis thereof for the person being interviewed may be performed from a short stand-off range, with the image sensors utilized being totally passive and covert.

With the increased need for employing detection systems and methods (e.g., deception detection methods and systems) in various field applications such as, for example, border control and airport checkpoints, generally, two technological components are desired. First, one or more methods and systems that can sense and compute human physiology at a distance in a highly automated fashion are desired. For example, one or more embodiments of such methods and systems are described in U.S. patent application Ser. No. 10/008,786, filed on Nov. 13, 2001, entitled, "System and method using thermal image analysis and slope threshold classification for polygraph testing;" U.S. patent application Ser. No. 10/008,392, filed on Nov. 13, 2001, entitled, "System and method using thermal image analysis for polygraph testing;" and U.S. patent application Ser. No. 09/776,470, filed on Feb. 2, 2001, entitled, "Detection system and method using thermal image analysis," all of which are incorporated herein by reference.

However, in addition to such methods and systems for sensing and computing human physiology at a distance and in a highly automated fashion, mechanisms that are appropriate for implementation of such methods and systems in various field applications are also required. One or more embodiments of such mechanisms are provided herein.

The present invention solves various problems related to the implementation of and/or application of such sensing and computing methods and systems in various fields (e.g., border or airport control checkpoints). For example, although the detection of deception can be highly automated, there still remains a problem with respect to who can be used to pose the questions to a person or subject being interrogated. Further, the subject's privacy in being interrogated also presents an issue. In a public area, like border control checkpoints, people are always close by (e.g., people waiting in the queue behind the subject). Such waiting persons may overhear the conversation the subject has with the security agent. Subjects that are shy by nature may feel intimidated by this procedure and exhibit traits that may be mistaken for false anxiety and/or result in an inaccurate determination of deception.

Further, typically, systems used to perform such deception detection include cameras, other sensors, calibrating and positioning devices, computers, and various amounts of cabling. If all of these components are exposed to the subject being interrogated, the subject may also feel intimidated, leading to contamination of any measurements taken therefrom. As such, according to the present invention, concealment of all or at least a substantial portion of the hardware necessary to carry out a deception detection examination procedure is employed.

Yet further, an open public area with a lot of noise and only partially controlled lighting, air currents, and temperature may pose a challenge in the operation of a detection system. For example, the noise may be distracting to the subject. Partially controlled environmental variables, like lighting, air currents, and temperature, may affect the accuracy of components of the thermal infrared-based detection system (e.g., the infrared camera). In addition, such factors may also alter the physiological parameters of a subject, affecting the performance of even a non-thermal-based detection system.

In many applications utilizing deception detection techniques, it is necessary to reconfigure and provide such detection systems in a mobile manner. As such, according to the present invention, the controlled environment detection systems, at least in one embodiment provided herein, are highly mobile and modular to accommodate space reconfigurations that are common in many applications (e.g., security checkpoints). Further, such detection systems according to the present invention blend well with the operation of the applications, such as security checkpoints.

To address one or more problems of the field of application for deception detection systems, the exemplary controlled environment detection system 10 includes an enclosure 12. The enclosure 12 may be of any size or shape suitable for carrying out the functionality as described herein. For example, at least a portion of the enclosure 12 must allow for a person to enter the enclosure and feel comfortable therein. Although the enclosure 12, as further described in one embodiment herein, is in the form of a rectangular modular structure, the present invention is in no manner limited to such a shape, but may be provided in any other number of suitable shapes.

Further, at least in one embodiment, the enclosure 12 is a portable structure that can be moved from location to location. For example, transport wheels 36 or any other transport mechanisms may be used to allow for ease of movement of the detection system 10.

Further, in one embodiment, the enclosure 12 is a portable structure that is of a size that can accommodate interrogation of a single individual but is incapable of interviewing multiple individuals (e.g., is of a size that would allow only a single individual to be comfortably seated therein). For example, the enclosure 12 may include only a single seat for a single individual.

Figure 2:
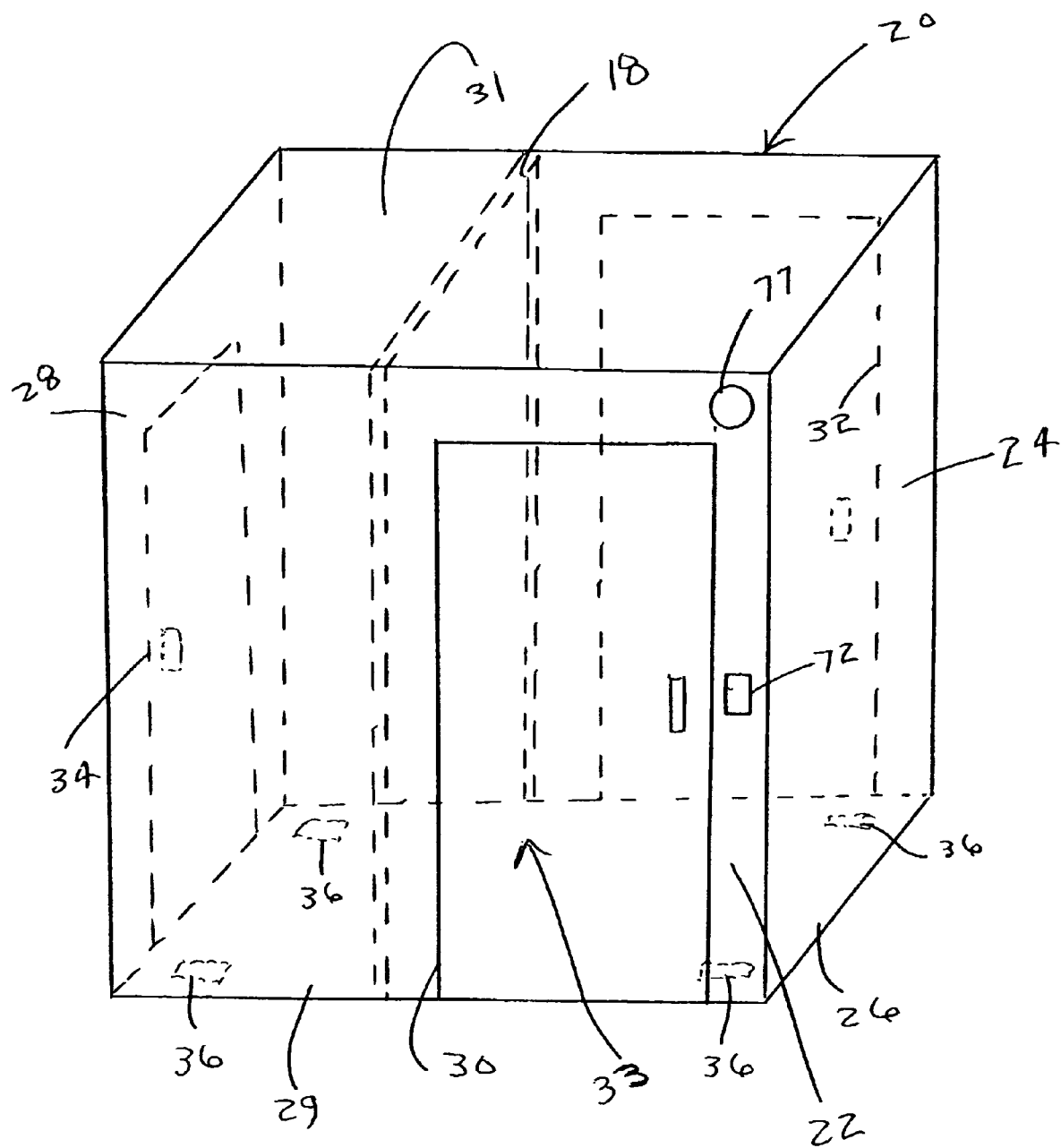
FIG. 2 is a general illustration of one embodiment of an outer shell of the detection system shown generally in FIG. 1 according to the present invention, including the location of several additional components of an exemplary embodiment of the detection system.

According to the illustrative embodiment shown in FIGS. 1 and 2, the enclosure 12 includes a first enclosed volume 14 and a second enclosed volume 16. The second enclosed volume 16 is physically separated from the first enclosed volume 14. For example, as shown in FIG. 1, the second enclosed volume 16 is physically separated from the first enclosed volume 14 by structure 18, as well as one or more other components of the detection system 10 (e.g., display 64, conditioning conduit 66, etc.). As used herein, physical separation of areas refers to the separation of areas where components contained in one area cannot be visually seen by an individual in the other area.

FIG. 2 shows one illustrative embodiment of an outer shell 20 of the enclosure 12, and further including several other selected components of the detection system 10 (e.g., selected for simplicity of description but not necessarily based on level of benefit provided thereby). As shown in FIG. 2, the outer shell 20 includes an entrance panel 22 and an exit panel 24.

Generally, the entrance panel 22 and the exit panel 24 are planar panels held in parallel relationship to one another by side panels 26, 28 (e.g., the side panels being orthogonal to the entrance and exit panels 22, 24). Further, the outer shell 20 includes a floor panel 29 and a top panel 31 for entirely enclosing an interior volume 33 defined by the enclosure 12.

The entrance panel 22 includes a closeable entrance door 30 sized to allow a person to enter the first enclosed volume 14. The closeable entrance door 30 may include any structure suitable for sealing off the first enclosed volume 14 when in a closed state.

Further, in one embodiment, the closeable entrance door 30 may be held in a locked state and access only permitted when authorized (e.g., automatically authorized such as with use of a document reader or manually authorized by an individual). For example, in yet a further embodiment, the lockable entrance door may be associated with an identification apparatus 72 coupled thereto (and/or to one or more other components of the system) which requires that a certain identification object (e.g., document) be used in order to enter the first enclosed volume 14 (e.g., entrance into the first enclosed volume 14 may be only granted with a subject's ticket stub or another form of identification capable of being read by the identification apparatus 72 that permits such access by releasing the door 30 from the locked state). Such identification information may also be provided to the computer system 60 for use in logging data or in the analysis of such data, as described with reference to FIG. 5 herein.

The exit panel 24 of outer shell 20 may include a closeable exit door 32 in one embodiment of the present invention. For example, the closeable exit door 32 may be any suitable structure for sealing the first enclosed volume 14 when the structure is in a closed state. For example, any latchable door may be used for the entrance and exit doors 30, 32. The exit door 32 may also be held in a locked state and exit only permitted when authorized (e.g., automatically authorized such as when an interrogation is over or manually authorized by an individual).

Figure 4:
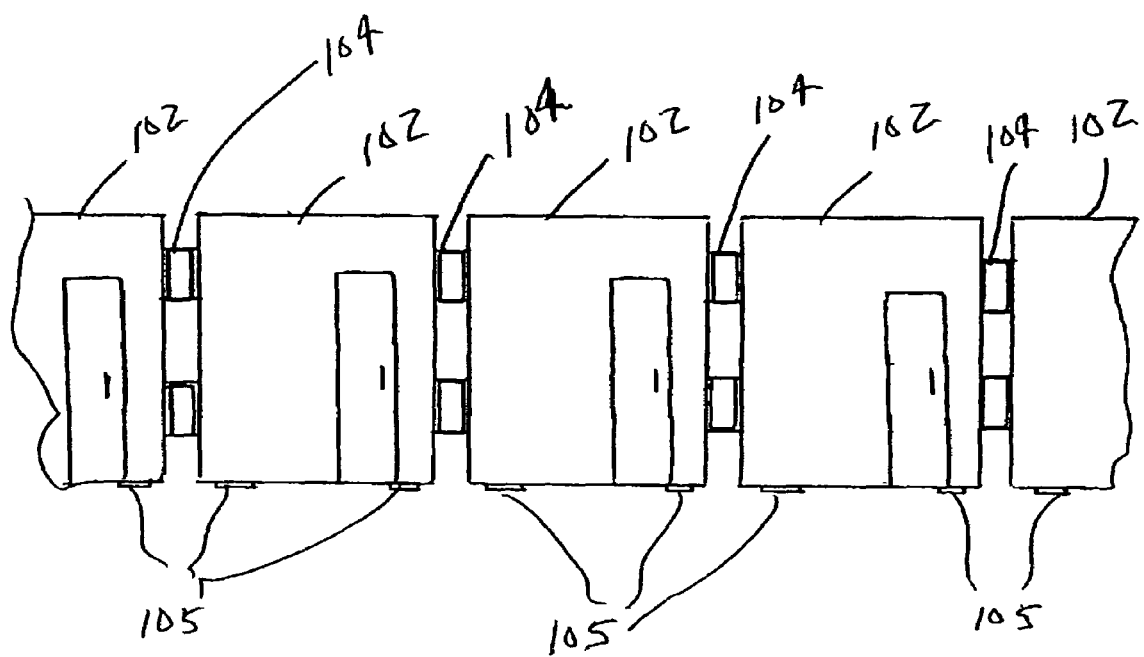
FIG. 4 is a general illustration of one embodiment of multiple modular enclosures positioned side by side to form a security checkpoint screening row according to the present invention.

By providing a closeable entrance door 30 and a closeable exit door 32, multiple enclosures 12 may be positioned side by side, as shall be described further with reference to FIG. 4. In such a configuration, a person may be allowed to enter the first enclosed volume 14 through closeable entrance door 30 and thereafter only allowed to exit the first enclosed volume 14 through closeable exit door 32.

Further, as shown in FIG. 2, side panel 28 includes an access door 34 to permit service personnel access to the various components of the controlled environment detection system 10 located within the second enclosed volume 16. Any suitable access entrance to the second enclosed volume 16 may be provided. For example, the access door 34 may be located on entrance panel 22 or exit panel 24 or even through top panel 31. In other words, any access to the second enclosed volume 16 is contemplated according to the present invention.

Likewise, entrance door 30 and exit door 32 may be provided in any fashion suitable to carry out the functionality of allowing a person to enter and exit the first enclosed volume 14 (e.g., one or both of the entrance and exit may be provided on the same panel, on side panel 26, etc.). However, in one preferred embodiment, the entrance door 30 and exit door 32 are on opposing panels of the enclosure 12 to permit the positioning of multiple enclosures side by side as shown and described with reference to FIG. 4.

Preferably, the outer shell 20 is constructed of one or more materials that provide a reduction of noise within the first enclosed volume 14. For example, such materials may include any noise insulating materials, multiple layers of materials with or without air gaps therebetween, etc. Further, for example, in one embodiment, the interior walls defining the first enclosed volume 14 are constructed of materials that are thermally neutral so as to prevent corruption of thermal imaging performed by the system. Likewise, all access doors to and from the first and second enclosed volumes 14, 16 are preferably of a sealed nature to further reduce the amount of noise that may enter such volumes.

As shown in FIG. 1, one or more components of the detection system 10 are positioned within the enclosure 12, e.g., within either first enclosed volume 14 or second enclosed volume 16. For example, an infrared camera 62, a computing apparatus 60, an air modification apparatus 65 (e.g., including conditioning conduit 66), along with portions of a display 64 are provided within the second enclosed volume 16.

Power 68 for one or more of the components in the first or second enclosed volumes 14, 16 is also provided. This power source 68 may be a standalone power source or may be provided through an interconnect to power outside of enclosure 12.

Generally, the various components located within the enclosure 12 can be described as components which assist in providing for control of one or more characteristics (e.g., lighting, air flow, temperature, etc.) of the environment within the first enclosed volume 14 or as components used in the monitoring and determination of the physiological state of a person (e.g., deception of the person when interrogated). However, some of the components such as the computing system 60 may be used for both purposes.

Figure 5:
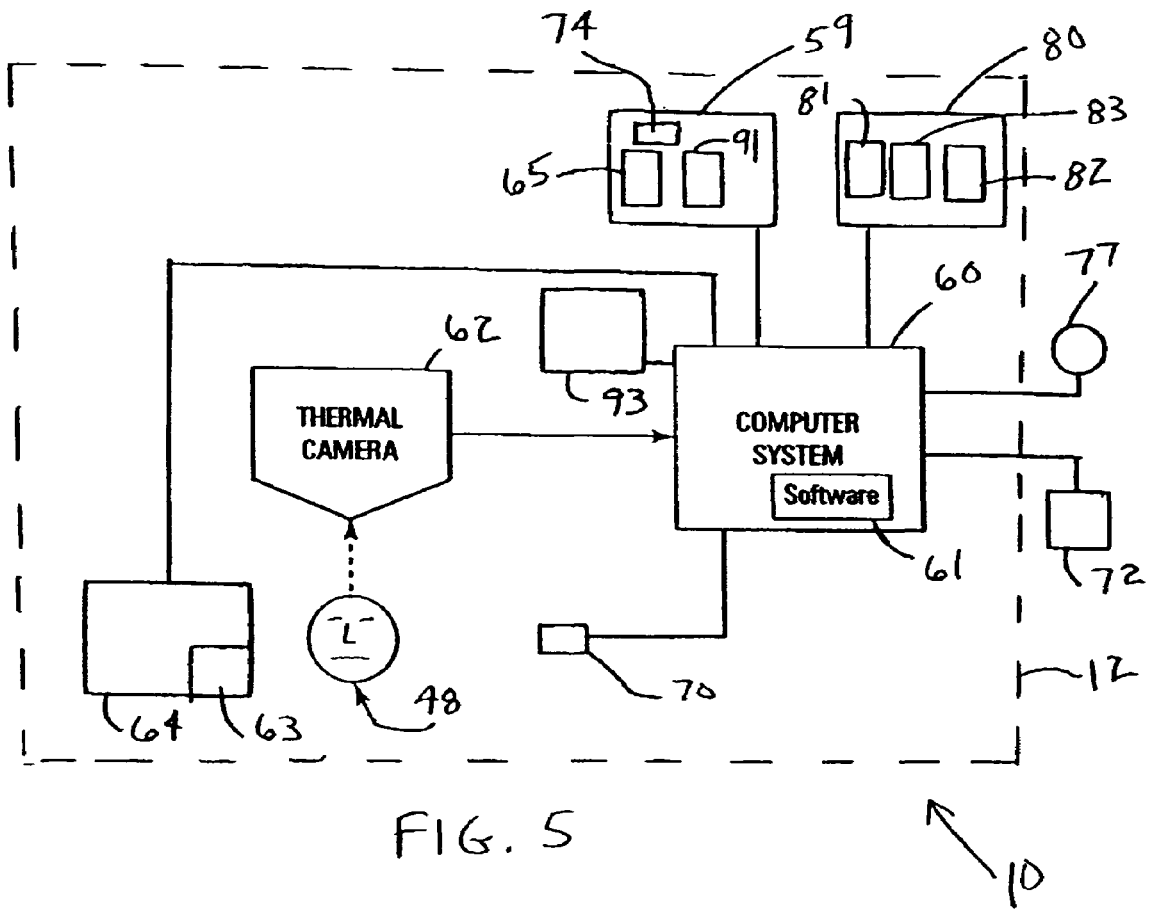
FIG. 5 is a block diagram illustrating one exemplary embodiment of a detection system according to the present invention.

FIG. 5 shows a block diagram of the exemplary detection system 10 including various components (many of which are also shown in the diagrams of FIG. 1 and FIG. 2) which may be advantageously used according to the present invention. Although all of such components are shown as providing particular advantages, according to the present invention, such components may be used in various combinations, and multiple embodiments are contemplated in which only some of the components are used while others are optional.

One skilled in the art will recognize that depending upon the detection process used, such components may vary. For example, only if thermal infrared image data is used is it necessary to employ a thermal infrared camera 62. Likewise, only if a speech synchronization process is used, as shall be described herein, is it necessary for a microphone 70 to be available for detection of a person's speech.

It is noted that although the present invention is described with respect to the specific use of thermal infrared image data for analysis and determination of a physiological state of an individual, that even non-thermal image data systems may benefit from the controlled environment detection system provided herein. Therefore, such systems and methods are also contemplated according to the present invention. However, the controlled environment is particularly advantageous for thermal imaging systems and methods due to the nature of the biometric information being captured from the individual (e.g., the controlled environment provides for less contamination in the information obtained by the system).

As shown in FIG. 5, a computer system 60 is provided that includes software 61 executable thereon for carrying out the functionality as described according to the present invention. The computing system 60, may be, for example, any fixed or mobile computer system, e.g., a personal computer. The exact configuration of the computer system is not limiting and most any device capable of providing suitable computing capabilities may be used according to the present invention. Further, various peripheral devices, such as a computer display, a mouse, a keyboard, a printer, etc., are contemplated to be used in combination with one or more processors of the computing system 60.

Further, for example, in one embodiment, the computing capabilities may be provided at a remote location (e.g., cable and/or wireless connections being provided between the processing apparatus at a remote location and the one or more components of the detection system 10 connected thereto). As such, only limited hardware would be provided in the second enclosed volume 16. For example, the monitoring may be performed remotely by a person monitoring several controlled environment detection systems 10.

Various components may provide input to or receive output from the computer system 60 via one or more ports or one or more suitable interfaces thereto. For example, as shown in FIG. 5, thermal infrared camera 62 provides thermal infrared image data of the face of a person 48 to computer system 60 for operation on and manipulation of such data. Further, the thermal infrared camera 62 may be controlled via computer system 62.

In one embodiment, both a far-infrared camera and a mid-infrared camera are used to provide thermal image data such that the data in the far-infrared band and the mid-infrared band may be compared to provide additional accuracy. However, one skilled in the art will recognize that either one or both of a far-infrared band and/or mid-infrared band camera may be used according to the present invention. Further, it is preferred that highly sensitive cameras be used when attempting to detect subtle changes in physiological response.

For example, the far-infrared camera provided under the trade designation ExplorIR may be used. It has a nominal temperature sensitivity of noise equivalent temperature difference (NETD) equal to 0.15° C. However, such performance is typically not obtained and the actual temperature sensitivity of the ExplorIR model may be above 0.5° C. As this is only a fair amount of facial temperature resolution, a certain amount of information may be masked thereby. The mid-infrared camera available from Raytheon under the trade designation Radiance HS Mid-Infrared Camera may also be used. It may be calibrated for a particular setting with nonlinear equations for improved accuracy. It generally has an NETD equal to 0.025° C. A calibration process may be complemented with a smart, highly accurate (0.01° C.) differential black body for near perfect scene temperature reference. Although several cameras are listed above, one skilled in the art will recognize that any suitable infrared camera may be used.

Display 64 is also coupled to the computer system 60, along with one or more speakers 63, to present one or more prerecorded questions to a person being interrogated within the first enclosed volume 14. For example, an animated or a video recorded figure may be used to present the one or more prerecorded questions to the person. The display 64 may be any suitable display for providing questions to or interrogating a person who is within the first enclosed volume 14. For example, the display 64 may be a large high definition flat panel screen or any other type of display apparatus (e.g., CRT display, computer screen, etc.). Likewise, the one or more speakers 63 may be used at one or more locations within the first enclosed volume 14. Any suitable speaker apparatus for providing an adequate level of sound to the person being interrogated may be used (e.g., speakers that are integrated with display 64 or standalone speakers).

Microphone 70 may also be located within the first enclosed volume 14 for receiving sound output from the person 48 being interrogated in the first enclosed volume 14 and providing an input representative thereof to the computer system 60. Any suitable microphone may be used, as well as any additional amplification circuitry or any other signal modification circuitry, which provides an adequate signal to the computer system 60 representative of speech of the person 48 being interrogated.

As an interrogation typically involves more than one question (although a single question interrogation is possible), with use of the microphone 70 detecting responses from a person 48 being interrogated, the questions being asked to the person 48 can be synchronized using speech understanding software that monitors the subject's responses. Such speech understanding software is shown generally in the software block 61 and may include any software operable to synchronize answers from the person 48 being interrogated with questions being posed to the person 48 via display 64 and speakers 63.

For example, in a synchronized interrogation process, the questions being asked may be delayed by a suitable period of time following a response by the person 48 being interrogated. Likewise, appropriate and specific questions may be tailored to be provided via the display 64 and speakers 63 depending upon a particular response provided by the person 48. For example, a "yes" answer to a question posed may trigger a different line of questioning than a "no" answer by the person 48 being interrogated.

During such interrogation, operation of the thermal infrared camera under control of computer system 60 acquires image data of at least the face of the person 48 being interrogated. With the person being interrogated being seated at a particular location within the first enclosed volume 14, focusing of the thermal infrared camera 62 on a region of the subject (e.g., the subject's face region) may be easily accomplished. However, the camera 62 may be provided on a single axis or a multiple axis apparatus for use in mechanically moving the camera, for example, horizontally and/or vertically, to track large movements of the person 48 being interrogated (e.g., movements that may take the person's face outside of the scene being imaged by camera 62).

The infrared camera 62 may be positioned behind a permissive infrared window 78 to hide the camera 62 from the person 48 being interrogated. This further reduces the intimidation of the person 48. In other words, a permissive infrared window 78 allows the camera 62 to record facial video of the person 48 being interrogated without the camera 62 being visible to the person 48.

Entrance identification apparatus 72, as shown in FIG. 5, may also provide an input to the computer system 60, as well as to provide authorization to an individual for access to the first enclosed volume 14 through entrance door 30. For example, the entrance identification apparatus 72 may be an information reader, such as a card reader, that may read one or more different forms of identification including, for example, a person's ticket stub, a form of identification (e.g., a passport or a driver's license), or any other identification documents that would show information regarding an individual's identity. This information may be provided to the computer system 60 for logging such identity, provide clearance checks (e.g., via a remote database), etc.

Yet further, an indicator 77 (such as, for example, a light, a buzzer, or any other apparatus for providing visual or sound indication) may provide input to or receive signals for control thereof from computer system 60. For example, the indicator may be used to show when an interrogation process is being performed (e.g., when the first enclosed volume 14 is being occupied by a person 48), as well as for showing when an interrogation of a person 48 is concluded. For example, the computer system 60 may control a light indicator 77 to indicate occupancy of the enclosure 12 (e.g., an lighted "occupied" sign).

Further, computer system 60 may receive input from one or more other physiological measurement apparatus 93 used to provide measurement of one or more additional physiological parameters (e.g., the same or another physiological parameter measured using the thermal image data being captured). As such, the physiological state of the person 48 being interrogated may be determined not only by using the thermal infrared data, but also with use of one or more other physiological parameters determined using measurements from the one or more physiological measurement apparatus 93. For example, pulse measurement devices, blood pressure measurement devices, near-infrared blood flow meters, etc. may be used in combination with thermal image analysis to determine whether a person is deceptive or is exhibiting anxiety in response to questions presented thereto. Such devices may provide for validation of a previously determined physiological state or may be used in combination with the thermal infrared image data to determine such a state.

Preferably, components of a system used for the interrogation of the person 48 in the first enclosed volume 14 are positioned within the second enclosed volume 16. At least in one embodiment, the computer system 60 is provided within the second enclosed volume 16. At least in another embodiment, the thermal camera 62 is provided within the second enclosed volume 16. Further, both the computer system 60 and/or the thermal camera 62 may be provided within the second enclosed volume 16, along with, other components such as cabling, air modification apparatus, etc.).

As shown in both FIG. 1 and FIG. 5, various environment control devices are used to control the environment within the first enclosed volume 14. For example, one or more sensors 80 may be positioned in one or more locations within the first enclosed volume 14 (e.g., a temperature sensor 81, an airflow sensor 82, or a light intensity sensor 83). One skilled in the art will recognize that various types of sensors may be used to detect and/or measure one or more characteristics of the environment within the first enclosed volume 14 and that the present invention is not limited to the particular sensors listed herein.

In one embodiment of the present invention, control of at least one of temperature, light intensity, and/or airflow is provided in the first enclosed volume 14. The output of the one or more sensors 80 may be provided to computer system 60 for control of one or more devices operable for adjusting temperature, light, or airflow. Further, one or more of such sensors 80 may also provide their output directly to one or more of the environmental modification apparatus 59 (e.g., light source 74, air conditioning apparatus 65 including conduit 66 and/or fan apparatus 91, etc.).

The lighting apparatus 74 may include any suitable light source. Preferably, light apparatus 74 includes a light source whose light intensity is controlled automatically. For example, such controllability may be provided through use of a light intensity sensor and/or computer system 60.

Air conditioning apparatus 65, including conduit 66 for use in providing conditioning of the air in the first enclosed volume 14 may take the form of any air modification apparatus, such as an apparatus for adjusting the temperature within the first enclosed volume 14. For example, such apparatus may include electric heat elements, air movement mechanisms or fans, air conditioning units, humidification units, heat exchange apparatus, or any other cooling or heating apparatus. Such air conditioning apparatus 65 again may be controllable via the computer system 60 and/or one or more sensors 80 (e.g., an airflow sensor 82 and/or a temperature sensor 81).

As shown in FIG. 4, preferably, each controlled environment detection system 10 is provided as a portable and modular structure. In other words, such systems may be easily moved from location to location and are each constructed or configured in substantially the same manner. As such, multiple controlled environment detection systems 102 (e.g., substantially similar to the controlled environment detection system 10, as shown and described with reference to FIGS. 1–2) can be positioned directly adjacent one another. As used herein, directly adjacent to one another refers either to them being in direct contact with or in close proximity to one another such that a person cannot proceed through the volume between the two detection systems 102. Further, for example, such detection systems 102 may be linked to one another using one or more linking mechanisms 104. For example, a latching mechanism or any other mechanisms available for attaching one of the detection systems to another may be used to form a line or row of the detection systems 102 through which an individual cannot traverse without going through one of the system enclosures.

Further, each of the portable and modular detection systems 102 is provided on a transport mechanism 105 (e.g., transport wheels) which allow for ease of reconfiguration of the detection systems 102. For example, if one portion of an airport is in need of more detection systems at a particular time, such portable and modular detection systems 102 can be moved from one location to another with ease. However, any other transport mechanism, including a forklift or any other portable structure moving apparatus, may be used to reconfigure a row of detection systems 102.

Figure 3:
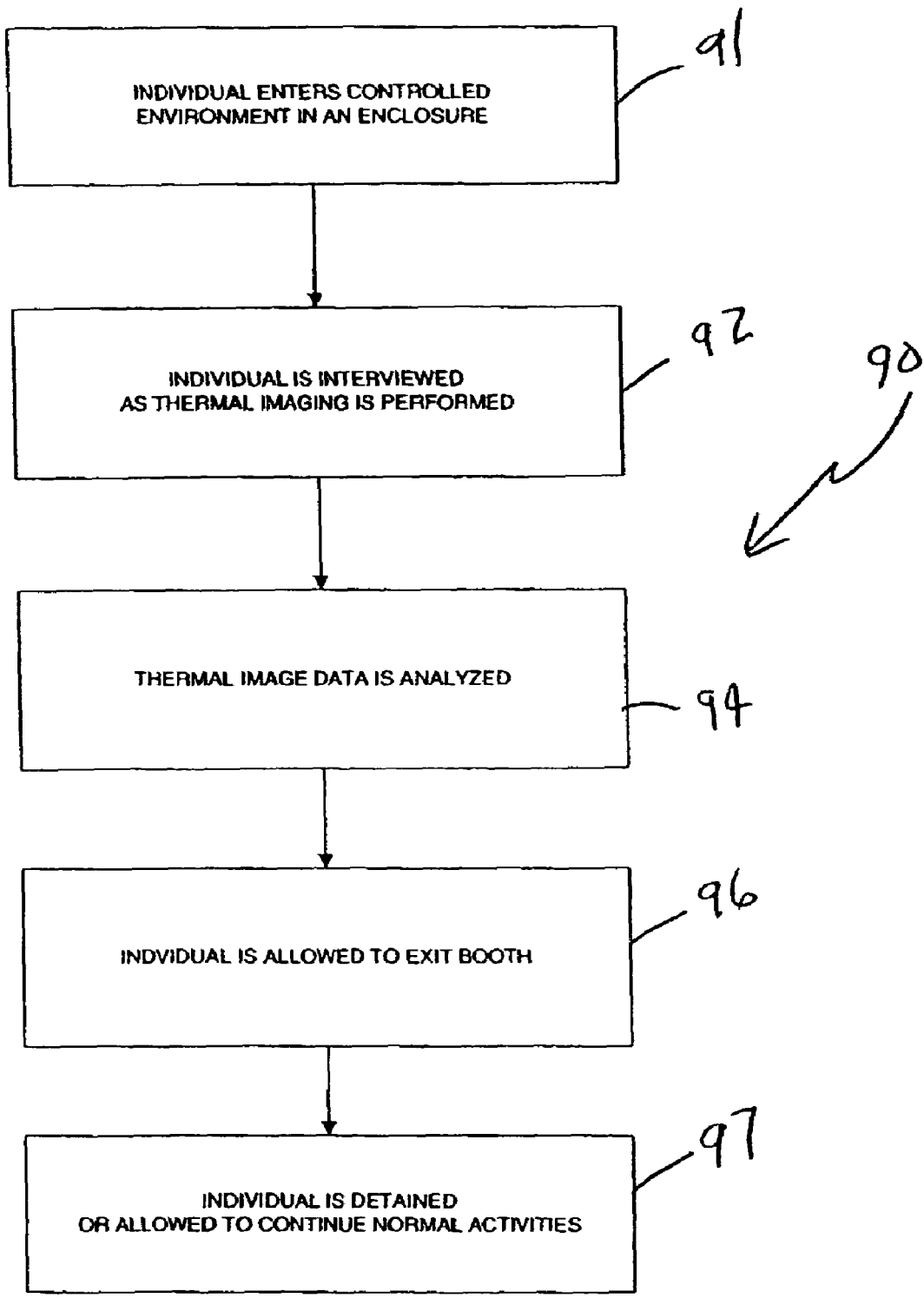
FIG. 3 is a generalized block diagram of one illustrative embodiment of a detection method according to the present invention.

Generally, one embodiment of a detection method 90 according to the present invention is shown in the block diagram of FIG. 3. An individual enters the controlled environment within the first enclosed volume 14 of enclosure 12 (block 91). For example, an indicator 77 positioned on the outer shell 20 of the enclosure 12 may signal the individual that the first enclosed volume 14 is unoccupied. The individual then enters the first enclosed volume 14 via the closeable entrance door 30.

In one exemplary embodiment of the method, for example, the individual may insert an identification document or card to be read by entrance identification apparatus 72 which unlocks entrance door 30 to allow the individual into the interior of first enclosed volume 14. The individual 48 then sits in the seat 50 within the first enclosed volume 14. In one embodiment, the individual may be instructed with use of the display 64 and/or speakers 63 to take a seat.

The seat 50 (e.g., the only seat in the first enclosed volume 14) may be any suitable structure for providing the individual 48 being interrogated in a proper position for recordation of thermal image data via infrared camera 62. For example, the seat 50 may be a built-in chair, a padded structure for providing the individual 48 with a comfortable setting, or any other suitable structure.

Further, the individual 48 may be requested to place an extremity next to or in a position adjacent physiological measurement apparatus 93 for providing measurement of another physiological parameter to be used for determining a physiological state of the individual 48 (e.g., for use in combination with the thermal image data captured via infrared camera 62).

The individual is then interviewed as thermal infrared imaging is performed (block 92). For example, the individual 48 is asked one or more questions so as to elicit a response therefrom. Such questions may be provided through use of the display 64 and speakers 63. Further, for example, a microphone 70 may detect a response from the individual 48 so that specific questions can be synchronized using a speech understanding system, as described herein.

The thermal image data captured during the interview may then be analyzed (block 94). For example, such thermal image analysis may be performed according to one or more different analysis methods, and the present invention is not limited to any particular thermal image data analysis method described herein. However, various analysis methods shall be described herein that may provide advantages when used in conjunction with the one or more controlled implementation techniques described herein.

After the interrogation is completed, the individual is allowed to exit the first enclosed volume 14 via closeable exit door 32 (block 96). For example, the display 64 and/or speakers 63 may be used to relay to the individual 48 being examined that the interrogation has been completed. The individual may then be allowed to exit the enclosure 12 to continue normal activities or the individual 48 is detained for further investigation (block 97). Even if the individual 48 is detained, the individual may still be allowed to exit the first enclosed volume 14 but may be subject to further interrogation after exiting. When the first enclosed volume 14 becomes unoccupied, the indicator 77 will notify any persons outside of the enclosure 12 that they may now proceed and enter the first enclosed volume 14.

One will recognize that various components of the controlled environment detection system 10 may be used to implement the method as described in FIG. 3 and provide additional environment control and monitoring features. However, for simplicity, and since such features have been described with respect to the system 10 of the present invention, all of such components as part of method 90 shall not be described in further detail.

One or more embodiments of the present invention shall now be described with relation to the structure and function of a booth (e.g., an enclosure 12 as described with reference to FIG. 1) by highlighting various solutions the controlled environment detection system 10 offers to various concerns that are relevant to the implementation of such a system in a field application (e.g., airport, border security checkpoint, etc.).

In one embodiment, to protect the subject's privacy and conceal detection equipment from the person being interrogated, the interrogation of the person is conducted inside a passport-type booth. This private room (e.g., the first enclosed volume) atmosphere will make the subject feel at ease and protect them from prying ears and eyes. At the same time, a convenient platform is provided to hide away what may be intimidating hardware in a closet space (e.g., the second enclosed volume 16) next to the private room.

In one embodiment, the thermal imaging hardware may be hidden in the closet space (e.g., the second enclosed volume) in front of the subject. A permissive infrared window at the top of the closet space may allow the camera to record facial video without being visible to the subject. The closet space can be used to place a large flat panel screen in front of the subject. The equipment in the closet space (e.g., the second enclosed volume 16) can be accessed and serviced from a door outside of the booth or enclosure 12.

In one embodiment, no actual examiners are used for interrogating the person. Rather, a virtual examiner is provided to interrogate a person. The virtual examiner may be provided by either an animated or video recorded figure. Different virtual examiners may apply depending on the cultural background of the person being interrogated to maximize the effectiveness of questioning. For example, the virtual examiner may provide a representation of a person on a display that is of the same cultural background, the interrogation may be performed in the native language of the person being interrogated, etc.

The use of a virtual examiner (e.g., a prerecorded examiner) provides a solution to various practical problems related to checkpoint questioning and establishes a reliable baseline. To enhance realism with respect to the use of such a prerecorded or virtual examiner, the use of a large high definition flat panel screen with stereo sound (e.g., that is located close to the subject) may be used. Further, as described herein, the replay of prerecorded clips for specific questions can be synchronized with a speech understanding system that will monitor the subject's responses. The virtual examiner interrogation process may be completely controlled through the computing apparatus 60 (e.g., a computing apparatus located within the closet).

The booth enclosure, at least in one embodiment, includes a chair where the subject will be seated for the short duration of the interview to relax and bring his/her physiology to a baseline level. The fact that the individual will be in touch with the chair can be used to obtain redundant physiological measurements (e.g., via physiological measurement apparatus 93) using one or more different sensors, such as one-dimensional polygraph sensors (e.g., near-infrared blood flow meter at the armrest of the chair).

Further, for example, in one particular embodiment, the soundproof nature of the booth does not only prevent others from overhearing the communication between the individual being interrogated and the virtual examiner, but also prevents any distracting noise to interfere in the subject's communication. In other words, for example, this not only improves the subject's psychology but also facilitates the operation of the speech understanding system used to synchronize responses and questions.

Yet further, in one embodiment, the booth is a very small space and its environmental parameters can be very accurately controlled with a climate control system (e.g., air conditioning apparatus including a fan, temperature sensors, etc.). Tight control of the environment will assure that the thermal regulatory balance of the subject is kept in check and any physiological changes will be due to parasympathetic responses and not due to environmental factors.

Controlled lighting in the booth provides a known source of noisy emission and reflectivity that can be accurately incorporated in the radiometric model for capturing thermal infrared image data. Further, such controlled lighting will allow the person being interrogated to comfortably watch the display 64.

Further, in one embodiment, the booth can be wheeled and therefore is highly mobile. A series of booths can be stacked one next to the other to form screening rows, much like metal detectors in airport gate entrances (see FIG. 4).

Entrance into the booth can be granted, or otherwise authorized, when the subject's ticket stub or form of identification (e.g., passport or driver's license) is slipped into and read by a card reader. Once a short interview is over, the door on the other side of the booth can open and allow the subject to exit towards the secure area. At the same time, a signal (e.g., light on) on the front side of the booth can clear the way for the next subject in line to approach. In this manner, subjects can be processed in a smooth manner and the operational flow can blend transparently into the functionality of the checkpoint.

Further, wheeled booths are easily transportable and can be rearranged easily within a checkpoint facility. Special latching mechanisms on the side may allow the booths to stack one next to the other and form screening rows, as described herein with reference to FIG. 4.

The implementation of the controlled environment detection system 10, as described with reference to FIGS. 1–5, provides for the determination of a physiological state of a person being interrogated (e.g., questioned). For example, as previously described herein, the physiological state being determined may include anxiety and/or deception. The controlled environment detection system 10 allows for implementation of one or more various thermal analysis methods (and apparatus corresponding thereto) in one or more different field applications (e.g., airport or border checkpoints).

One or more of such methods are described in U.S. patent application Ser. No. 10/008,786, filed on Nov. 13, 2001, entitled, "System and method using thermal image analysis and slope threshold classification for polygraph testing;" U.S. patent application Ser. No. 10/008,392, filed on Nov. 13, 2001, entitled, "System and method using thermal image analysis for polygraph testing;" and U.S. patent application Ser. No. 09/776,470, filed on Feb. 2, 2001, entitled, "Detection system and method using thermal image analysis."

For example, in U.S. patent application Ser. No. 09/776,470 methods and systems for detecting anxiety through thermal facial image analysis are described. In general, the change in thermal facial image signature of an individual is used to determine whether the individual is experiencing anxiety. For example, as described therein, anxiety is accompanied by an increased local warming around the individual's eyes. This change in facial thermal pattern around the individual's eyes is typically accompanied by a concomitant cooling over the cheeks and/or concomitant warming over the carotid artery region.

Generally, this pattern of thermal change in an individual's body during an onset of anxiety (e.g., the change in the individual's thermal signature during onset of anxiety) makes physiological and evolutionary sense, as it represents a mechanism to facilitate rapid eye movement during preparedness for flight. In other words, elevated anxiety precipitates a host of physiological responses, many of which result from altered sympathetic nervous system activity. One of these responses is local redistribution of blood flow resulting in abrupt changes in local temperatures at various regions in the individual. Such changes in local temperatures in such regions are readily apparent in the human face where the layer of flesh over bone is relatively thin.

Such abrupt temperature changes in localized regions can be detected by human face emissions in both the mid-infrared thermal band (i.e., 3 microns to 5 microns band) and far-infrared thermal band (i.e., 8 microns to 14 microns band) of the electromagnetic spectrum. As one skilled in the art will recognize, such ranges may be slightly shorter or longer.

Figure 6:
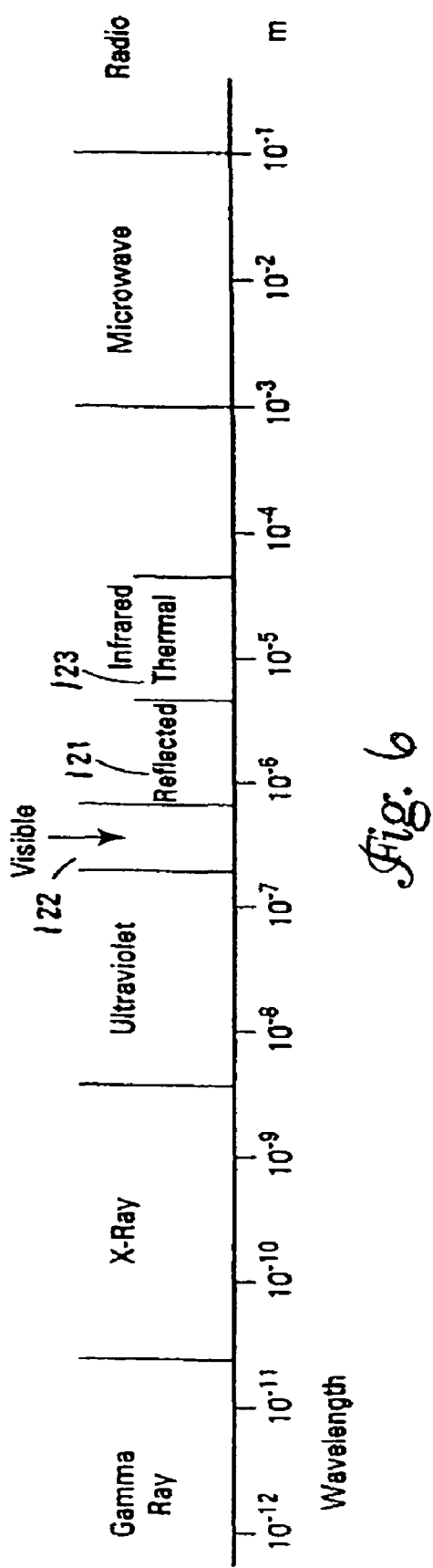
FIG. 6 is a graph of the electromagnetic (EM) spectrum.

A graph of the electromagnetic spectrum is shown in FIG. 6, with the thermal infrared band shown as reference numeral 123. The thermal infrared band lies above the visible band 122 and reflected infrared band 121 of the electromagnetic spectrum.

As such, thermal infrared detectors suitable to sense temperature variations in such regions of the spectrum can be used to produce thermal facial images, or thermograms, representative of such local temperature changes in the human face of an individual. Such data of the thermograms (e.g., those using either one or more of the mid-infrared band and far-infrared band) may be used to determine a physiological state of the individual (e.g., anxiety), as described in U.S. patent application Ser. No. 09/776,470, which is incorporated herein by reference.

For example, as described in U.S. patent application Ser. No. 09/776,470, and as described herein with reference to FIG. 7, a thermal facial image of an individual 48 with reference to various regions of the individual's face 130 provide an individual signature that can be detected as anxiety. For example, as described above, an onset of anxiety in the individual 48 (e.g., such as that which may be induced by a startling stimulus, induced when answering questions or being interrogated, induced by fear when smuggling goods into a country, induced by fear arising from the need to establish an escape route when proceeding with covert operations in a secret area, etc.) is associated with a warming due to increased blood flow in the periorbital region 134 around the eyes 135 of the individual 48. The periorbital region size varies with the individual 48. This extra blood flow to the eye musculature in the periorbital region 134 is primarily redirected from the cheek regions with a corresponding cooling indicated therein.

With the above changes in temperature in the localized regions of the individual's face 130 that accompany an onset of anxiety, and with suitable monitoring of emissions from the individual 48 in the thermal infrared spectrum from before the time of anxiety onset (e.g., a thermal history) and also after the time of onset, detection of transition from a prior state, e.g., a calm state, to an anxiety state can be achieved. This change in facial thermal infrared pattern or signature at the time of the transition is dramatic and can be easily recognized as described in U.S. patent application Ser. No. 09/776,470.

However, in many circumstances, for example, in a deception detection (e.g., a polygraph test) setting, when thermal image data is obtained, temperature changes observed around the eyes and in the face in general may only be subtle and not abrupt as described in the onset of anxiety with reference to U.S. patent application Ser. No. 09/776,470. As such, although anxiety may be detected in detection system 10 using the methods and systems described in U.S. patent application Ser. No. 09/776,470, when viewing only thermal image data as illustrated further below, such temperature changes may be almost unnoticeable. Such disparity between the thermal image data changes due to anxiety and those due to polygraph testing (e.g., deception detection) are likely a result of the only subtle stress imposed on polygraph subjects.

Figure 9A:
FIGS. 9A–9B and FIGS. 10A–10B illustrate a comparison between thermal image data and thermal image data transformed to blood flow rate data according to one or more illustrative embodiments of thermal image data analysis processes such as those shown generally in FIG. 3 according to the present invention.
Figure 9B:
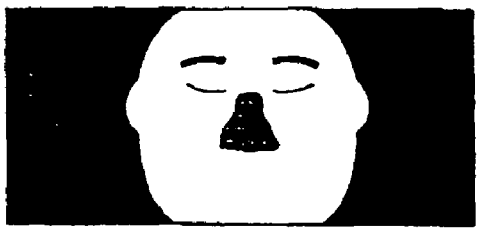

Such unnoticeable temperature changes in the thermal image data obtained during polygraph testing is shown generally in FIGS. 9A–9B. FIG. 9A shows thermal image data of a person prior to and at the beginning of responding deceptively to a question in a polygraph test. The temperature is visualized in gray scale, although any visualization scheme could be used, e.g., rainbow coloring scheme with higher temperatures represented by bright colors such as yellow and lower temperatures represented by other colors such as blue. FIG. 9B shows visualized thermal image data of a person towards the end of the person's deceptive response to the question. As can be seen in FIGS. 9A–9B, no noticeable difference in thermal image data appears.

Figure 10A:
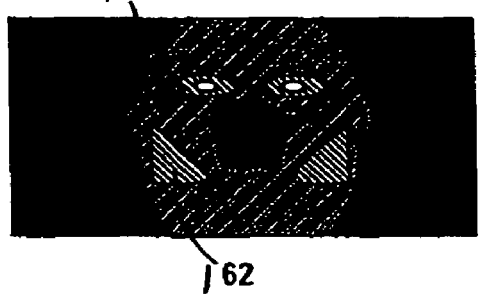
Figure 10B:
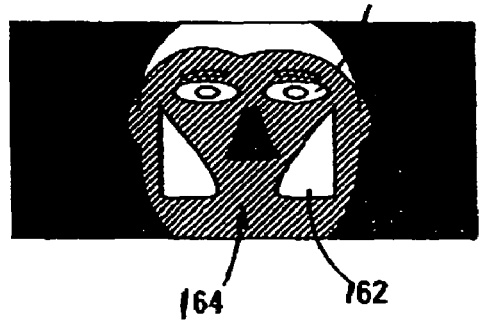

As such, to provide for useful information according to one embodiment of the present invention for use in polygraph or deception testing, the thermal image data is transformed to blood flow rate data as described further herein and as visualized in FIGS. 10A–10B. In FIG. 10A, corresponding to the thermal image data of FIG. 9A, visualization of blood flow rate in a person prior to and at the beginning of a deceptive response to a question is shown generally as a very dark image. Lighter regions 160, 162 may be generally seen in the periorbital region 160 of the face and the cheek region 162 of the face. This is indicative of changing blood flow rate in such areas.

Towards the end of the person's deceptive response to the question, visualization of blood flow rate in the person's face corresponding to the thermal image data shown in FIG. 9B is provided in FIG. 10B. As shown in FIG. 10B, the change in blood flow rate in the periorbital region 160 is visualized as much lighter relative to that shown in FIG. 10A. Likewise, cheek region 162 is also visualized in a much lighter manner, as is a majority of facial skin 164, when compared to that of FIG. 10A.

The difference in the visualization of blood flow rate data between FIG. 10A and FIG. 10B is significant. The differences shown in the visualization of blood flow rate intensities are represented in such Figures with the lighter or brighter regions indicating the highest degree of change in blood flow rate. In other words, as the response to the question is answered deceptively, the change in blood flow rate from the time prior to the question to a time during the deceptive response is visualized in the Figures by the lighter representation of the face in FIG. 10B versus that shown in FIG. 10A.

Such differences between FIG. 10A and FIG. 10B are in direct contrast to the lack of differences in the visualized raw thermal image data shown for such individuals in FIGS. 9A–9B. As a result, with amplification of the thermal image data (e.g., transformation of such thermal image data to change in blood flow rate over a plurality of frames of thermal image data), determination of whether a person's response to a question is deceptive or non-deceptive can be attained as described in U.S. patent application Ser. Nos. 10/008,786 and 10/008,392, both of which are incorporated herein by reference.

In view of the preceding generalities, one or more embodiments of a detection system 10 can incorporate such thermal image analysis methods described therein for determining whether a response by an individual (e.g., a statement by an individual) is deceptive or non-deceptive (e.g., whether a person is being deceitful or truthful). The computer system 60 for providing such analysis is operable to execute software that provides for the determination of the deceptive or non-deceptive state of a person based on thermal image data transformed to blood flow rate data.

The computer apparatus 60 includes software components 61 for operation on thermal facial image data provided from one or more thermal infrared cameras 62. One or more of such software components 61 may be used to operate on the thermal image data, e.g., pixel data, provided from the thermal infrared camera 62 to determine whether an individual 48 is non-deceptive or deceptive with respect to an elicited response therefrom. Such algorithmic software components for analysis of the thermofacial images of an individual 48 are shown as a part of an exemplary flow or block diagram of the thermal data analysis method 150 (i.e., polygraph method) shown in FIG. 8.

Figure 8:
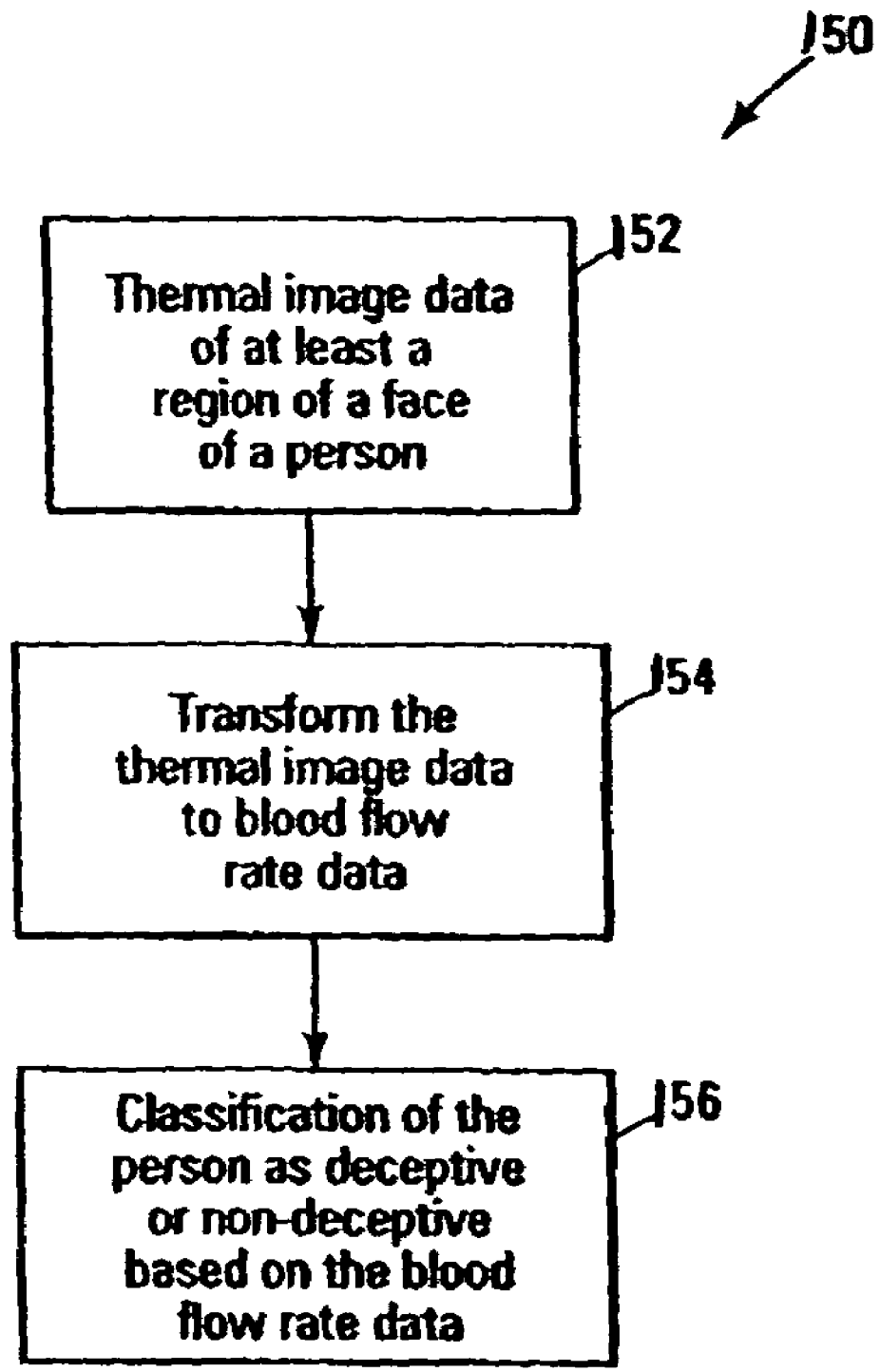
FIG. 8 is a general block diagram illustrating one exemplary embodiment of a thermal image data analysis process such as that shown generally in FIG. 3 according to the present invention.

As shown in the polygraph or deception detection method 150 of FIG. 8, thermal image data 152, e.g., pixel data, of a scene in which the individual 48 is located is provided to the computer apparatus 60 and is thereafter operated upon by software 61. Such software 61 includes at least a transformation component (block 154) for transforming the captured thermal image data for a person to blood flow rate data and a classification component (block 156) for classifying the person as deceptive or non-deceptive based on the blood flow rate data.

Generally, transformation component 154 provides an algorithm to transform thermal image data of the face of an individual 48 to blood flow rate information (e.g., blood flow rate, change in blood flow rate over time, etc.) embodied as blood flow data. Preferably, such transformation changes the thermal image data into data representative of the change of blood flow rate over time (i.e., over a plurality of frames) of one or more regions of the face.

Figure 7:
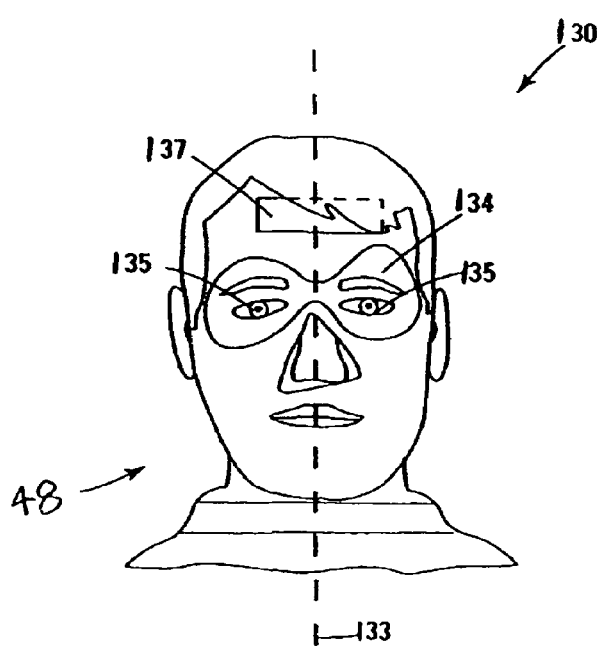
FIG. 7 is a diagram of an illustrative thermal facial image according to the present invention.

Such transformation may include any number of different processing techniques. For example, such transformation may include segmentation algorithms to separate thermal image data of the face from background of the thermal image data of the scene provided from camera 62. Likewise, a face partition component may provide the ability to partition the thermal image data of the face into one or more regions. In one exemplary embodiment, as shown in FIG. 7 and as described herein, the periorbital region 134 is preferably used according to the present invention.

It will be recognized by one skilled in the art that any number of regions may be used in the deception detection method described herein, e.g., the periorbital region, the cheek region, a forehead region, a nasal region, etc. However, certain regions may provide more beneficial information relative to the others. Further, as described elsewhere herein, blood flow rate for one or more points of one or more regions of the face (e.g., a network of points) may be used to provide true two-dimensional blood flow rate data for polygraph testing.

Further, generally, the classification component (block 156) provides an algorithm operable upon the transformed thermal image data to determine whether an individual 48 is being deceptive or non-deceptive. For example, automatic classification of the individual 48 into a deceptive or non-deceptive classification may be performed. Such classification may be performed by one of various types of classification algorithms such as, for example, a pattern recognition algorithm that is a part of a class of algorithms using statistical learning methodology. Such algorithms, for example, may be used to correct for some variability in the thermal signatures across the human race. Further, for example, as further described herein, baseline and/or threshold based classification techniques may be used.

Therefore, generally, the polygraph method 150 as shown in FIG. 8 includes the provision of thermal image data of at least a region of the face of a person (block 152). The thermal image data of at least the region of the face of a person is transformed to blood flow rate data (block 154). Thereafter, the blood flow rate data is used for classification of the person as being deceptive or non-deceptive (block 156), for example, with respect to a response elicited from the person.

Figure 11:
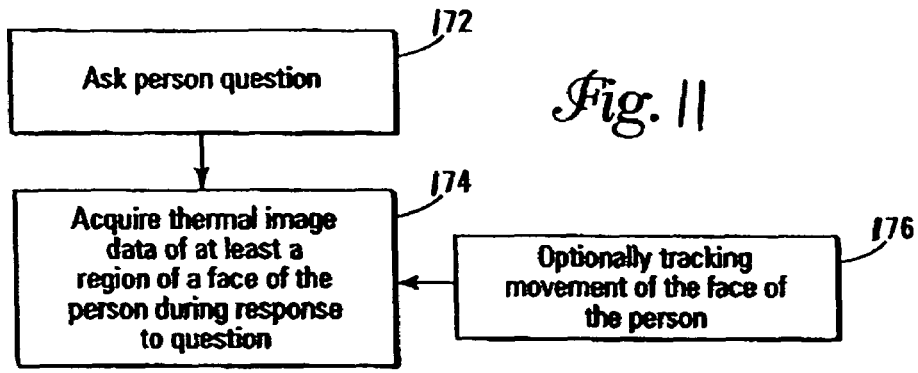
FIG. 11 is one illustrative exemplary embodiment of thermal image acquisition shown generally in FIG. 3 according to the present invention.

FIG. 11 is one illustrative embodiment of acquisition of thermal image data shown generally in block 152 of polygraph method 150 in FIG. 8. Generally, as shown in FIG. 11, a response from a person is elicited by asking the person a question (block 172). Thermal image data of at least a region of the face of the person asked the question is acquired during at least the response to the question (block 174) (e.g., thermal image data may be captured during the question, during the response, after the response, etc.). For example, thermal image data of at least a region of the face in a scene is received from a thermal infrared camera, e.g., thermal infrared image device 62. Such thermal image data includes pixel data of at least one frame of the scene. Preferably, however, a plurality of frames are provided from the thermal infrared camera.

The pixel information may be either in the form of digital values or direct temperature readings. Of course, the digital values are proportional to the actual scene temperatures at the respective points or pixels. In other words, pixel values have either indirect or direct correlation to scene temperatures. This is in contrast to visible band images, where pixel values have direct correlation to reflectance values.

Such received thermal image data representative of the thermal characteristics of a scene may be directly displayed and/or stored by the computing apparatus 60. For example, software associated with computing apparatus 60 may allow for the direct display of such data in degrees centigrade. For example, in many commercial systems, such data may be provided in grayscale values. Such grayscale display of images may generally have a poor visualization affect. Other commonly employed rainbow or pseudo-coloring display schemes may have relatively better imaging quality but achieve optimal results for the dynamic range of the visible band of the electromagnetic spectrum.

Optionally, at least the face of a person, e.g., the human head, can be tracked in the scene as it moves around during the length of polygraph testing as the thermal image data is being acquired. Such tracking is preferable, as an accurate solution of the differential thermodynamic equation for transforming thermal image data to blood flow rate data operates point-wise and across frames. However, although tracking provides for a more accurate determination of deceptive versus non-deceptive behavior by the person, the present invention may be performed assuming a completely stationary subject for short periods of time.

With a face tracking algorithm in place, a network of points of the face can be developed where blood flow rate can be monitored over time. This is true two-dimensional information as opposed to pseudo two-dimensional information, e.g., average blood flow over a region of pixels. However, averaging blood flow rate in the periorbital area, or over a substantial facial area is tolerant to registration errors and is a practical alternative to use of a head tracking algorithm and/or the use of a network of points process.

Thermal image data may be acquired for one region of the face, e.g., periorbital region 134 of an individual 48, as shown in FIG. 7, or may be acquired for a plurality of regions. As indicated above, blood flow rate over a substantial facial area may be more tolerant to registration errors.

The thermal image data of the scene may be operated upon by a segmentation algorithm as previously mentioned to separate a person's face from background of the scene captured. For example, the segmentation process may compare thermal image data from at least one region of the scene to thermal image data of another region of the scene. As the thermal characteristics of the human face are usually well contrasted to those of the background, such comparison and segmentation can be easily implemented. The comparison results in data which can be used to separate the human face from the background. The thermal image data of the human face separated from the background can then be used in later processes, e.g., by a transformation component (block 154 in the polygraph method 150 of FIG. 8).

Further, partitioning of the face may also be provided by comparing thermal image data of one region to thermal image data of another region to distinguish particular regions from each other. For example, the underlying anatomical features of the face 130 facilitate orientating the face 130 for partitioning.

For example, as shown in FIG. 7, the face 130 is bilaterally symmetrical about plane 133 (defined through the face 130, e.g., orthogonal to the FIG. 7) and aids partitioning into regions of interest, e.g., one eye in each half of the face, the nose lying half on one side of the plane 133 and half on the other side of the plane 133, etc. As such, generally, there is also symmetry of thermal image data from one side of the face to the other side.

One can achieve demarcation or partitioning of the facial regions using various algorithm methods. For example, a region competition algorithm derived by minimizing the generalized Bayes/MDL criterion using variational principle may be used for such demarcation of the facial regions. Such algorithms are described in an article by S. C. Zhu and A. Yuille, entitled "Region Competition: Unifying Snakes, Region Growing, and Bayes/MDL for Multiband Image Segmentation," IEEE Transactions on Image Analysis and Machine Intelligence, Vol. 18, No. 9 (September 1996).

Preferably, the segmentation and partitioning algorithms should be able to perform on static images as well as on dynamic sequences of images, e.g., video clips, live video feeds, etc. As such, in the case of image sequences, e.g., dynamic image sequences provided in a real-time fashion, a thermal statistic/tracking and update component may be used to lock onto the face and/or one or more of the segmented or partitioned regions of interest. Such segments or regions of interest may then be tracked from frame to frame with the particular thermal image data noticed or identified immediately. Further, data from multiple images may be used to provide accurate and effective thermal image data of one or more regions of interest. The thermal image data of one or more of the regions of interest, e.g., the periorbital region, the cheek region, etc., provide information that can be used for classification by the classification component (block 156 as shown in the polygraph method of FIG. 8).

In other words, thermal image data acquisition block 152 may be used to continuously lock onto the face and the segmented or partitioned regions of interest therein from frame to frame throughout a period of time. The thermal image data of one or more of the regions obtained throughout this dynamic tracking can be updated dynamically from frame to frame to provide the necessary thermal image data for use according to the present invention. The various processes described above, e.g., segmentation, partitioning, etc., either together or one or more thereof, may operate as preprocessing routines to provide thermal image data for transformation thereof to blood flow rate data. Such blood flow rate data may then be used for classification (block 156).

One skilled in the art will recognize that various preprocessing routines may be performed with respect to the thermal image data prior to providing such thermal image data for transformation to blood flow rate data and that the present invention is not limited to only those briefly described herein.

The transformed blood flow rate data based on the thermal image data may be used alone (i.e., as a sole physiological parameter) for classification of a person as deceptive or non-deceptive with respect to an elicited response therefrom (classification block 156 in the polygraph method 150 shown in FIG. 8). However, such transformed blood flow rate data may also be used in combination with one or more other physiological parameters different than blood flow rate data obtained using thermal image data as shown and described with reference to FIGS. 12 and 13.

Figure 12:
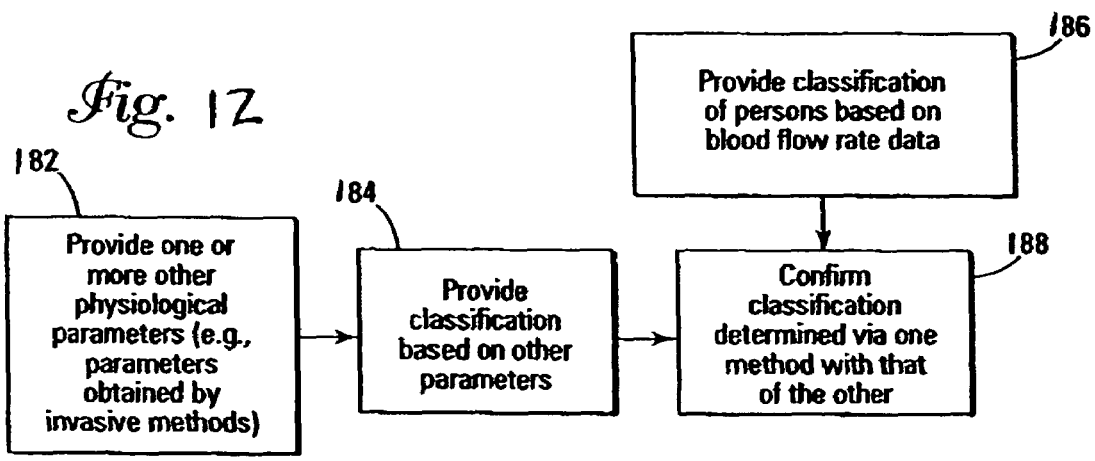
FIG. 12 is one illustrative block diagram of a classification method according to the present invention using physiological parameters different than, and in addition to, using thermal image data.

FIG. 12 provides for classification of a person's elicited response as non-deceptive or deceptive based on blood flow rate data as shown by block 186. For example, such classification may be the result of the polygraph method 150 as shown in FIG. 8. In addition, a classification of the person's elicited response as deceptive or non-deceptive is also provided based on other physiological parameters (block 184).

For example, polygraph testing is a standard procedure that conventionally has used one or more physiological parameters to determine whether a person's answers to questions are deceptive or non-deceptive, i.e., deceitful or truthful. During such conventional polygraph testing, physiological parameters such as blood volume and pulse change, respiratory changes, and electro-dermal activity have been recorded using invasive techniques and are then used for determining truthfulness of a person. The present invention as shown in FIG. 12 uses one or more of such other physiological parameters, i.e., physiological parameters obtained by invasive methods that are different from blood flow rate data obtained according to the present invention using thermal image data, to classify an individual as deceptive or non-deceptive. For example, as shown in FIG. 12, such other physiological parameters are provided as shown in block 182 and the classification is performed based on such parameters in block 184.

Thereafter, the classification of whether the person is being deceptive or non-deceptive based on blood flow rate data obtained using thermal image data (block 186) may be used to confirm the classification of an individual based on one or more other physiological parameters provided to the process (block 182 and block 184). Likewise, the classification based on blood flow rate data obtained using thermal image data (block 186) may be confirmed using a classification resulting from the measurement of the other physiological parameters different than blood flow rate data obtained using thermal image data (blocks 182 and 184).

Figure 13:
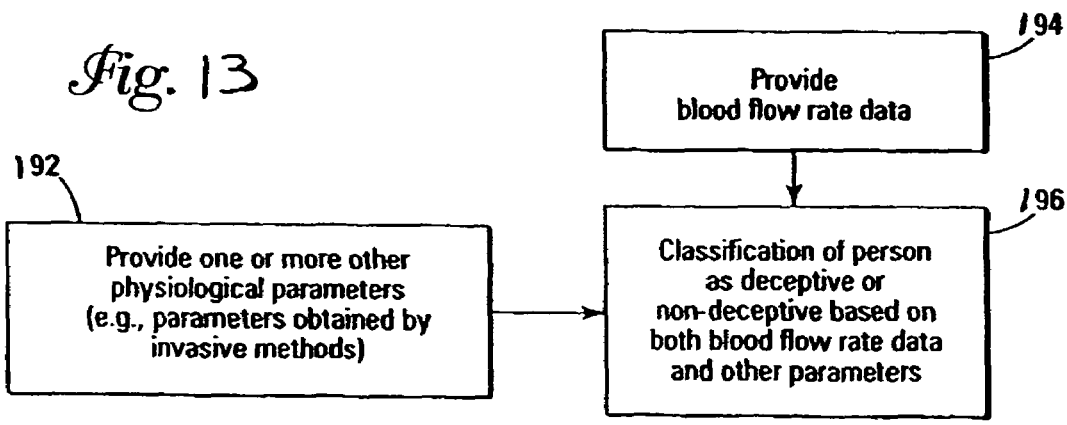
FIG. 13 shows another illustrative block diagram of a classification method using one or more other physiological parameters, in addition to using thermal image data according to the present invention.

Also, as shown in FIG. 13, both blood flow rate data (block 194) and one or more other physiological parameters different than blood flow rate data obtained using thermal image data (block 192) may be provided to a classification algorithm. Classification of a person as deceptive or non-deceptive may be based on both the blood flow rate data obtained using thermal image data and the one or more other physiological parameters, e.g., parameters obtained by invasive methods. For example, an algorithm taking both data gathered noninvasively and data gathered invasively into consideration when arriving at a classification may be used.

One skilled in the art will recognize that classification based on blood flow rate data obtained using thermal image data may be used for any other purpose in polygraph testing. For example, confirmation of other classifications, use in classifying individuals, preliminary determinations of deception or non-deception may be used to invoke other applicable polygraph testing methods or steps, etc.

Further, blood flow rate data determined according to the present invention may be used for other beneficial purposes other than polygraph testing. For example, monitoring of the blood flow rate data determined according to the present invention may be used for a particular medical application, e.g., control of a process or apparatus based on the monitored data. In other words, the transformation of thermal image data to blood flow rate data according to the present invention is a unique manner of attaining blood flow rate information to be used in other types of processes or apparatus.

Further, just as described in U.S. patent application Ser. No. 09/776,470, the present invention may be used to detect other physiological states of a person through the analysis of the thermal image data including the transformation to blood flow rate data. For example, in addition to deceptive versus non-deceptive determinations, the methods and systems described herein may be used to determine one or more different physiological states of a person, e.g., depression, periods of dementia, anxiety, etc.

Figure 14:
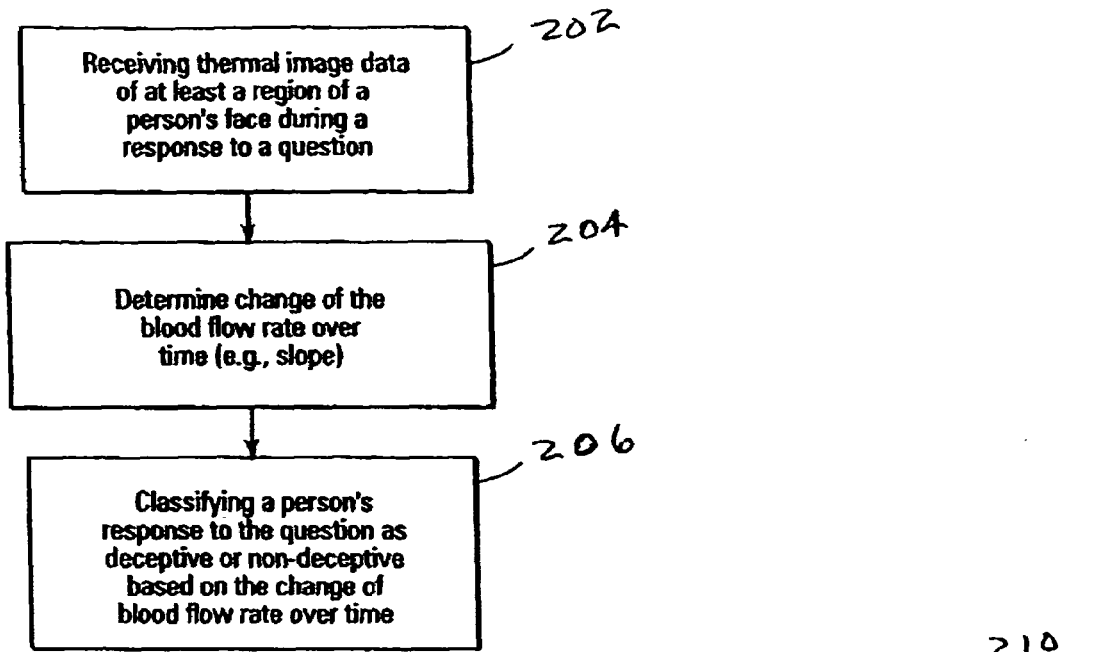
FIG. 14 shows an exemplary embodiment of a thermal image data transformation process and classification process generally shown in the method of FIG. 8.

FIG. 14 shows one exemplary embodiment of a flow diagram for transformation component (block 154) in combination with classification component (block 156) of the polygraph method 150 shown in FIG. 8. As shown by block 202, thermal image data acquired via the thermal image acquisition component 152 of polygraph method 150, as shown in FIG. 8, is received for at least a region of a person's face during at least an elicited response to a question. Such thermal image data has been described previously herein.

Thereafter, change of the blood flow rate over time (e.g., slope) is then determined based on the thermal image data (block 204). In other words, slope representative of the change of blood flow rate over time for thermal image data received from the thermal infrared image device (e.g., device 62 of the deception detection system 10 of FIG. 1) is determined.

Such blood flow rate change over time can be determined from the thermal image data as described below. The fluctuation of temperature in the various facial areas is primarily due to the changing blood flow rate.

Thermodynamic modeling shows that the blood flow rate is inversely proportional to the square of the skin temperature deviation from the temperature at the core of the human body. This nonlinear relation amplifies the weak temperature change patterns observed in polygraphy subjects and brings the information noise down to levels such as that described in the anxiety determination application, U.S. patent application Ser. No. 09/776,470.

Specifically, at thermal equilibrium, one can model the heat balance equation for human skin tissue as:

$$Q_r + Q_e + Q_f = Q_c + Q_m + Q_b,$$

where
$Q_r$=the heat radiated from the subject to the air in units of calories;
$Q_e$=the basic evaporated heat;
$Q_f$=the heat loss via convention into the air neighboring the skin surface;

$Q_c$=the heat conducted by subcutaneous tissue;
$Q_m$=the heat corresponding to the metabolic rate of cutaneous tissue; and
$Q_b$=the heat gain/loss via convection attributable to blood flow of subcutaneous blood vessels.

Observing skin temperature change ($\Delta T_s$) in a short period ($\Delta t$), the following equation results:

$$C_s \Delta T_s = -(\Delta Q_r + \Delta Q_e + \Delta Q_f) + (\Delta Q_c + \Delta Q_m + \Delta Q_b),$$

where $C_s$=the heat capacity of skin.

For short periods of time ($\Delta t$), and assuming that the subject did not recently have a sizeable meal, one can consider the term $\Delta Q_m$ as negligible. The terms $\Delta Q_r$, $\Delta Q_e$, and $\Delta Q_f$ are shown to be of magnitude approximately 1/100 less than the magnitude of $\Delta Q_b$. Therefore, $$C_s \Delta T_s \sim \Delta Q_c + \Delta Q_b$$

$$= \alpha p_c V_{S_2}(T_B - T_{S_2})S - \alpha p_c V_{S_1}(T_B - T_{S_1})S + K_c(T_B - T_{S_2})/(3d) - K_c(T_B - T_{S_1})/(3d)$$

$$= \alpha p_c \Delta V_S T_B S - \alpha p_c (V_{S_2} T_{S_2} - V_{S_1} T_{S_1})S - K_c \Delta T_S/(3d)$$

$$= \alpha p_c \Delta V_S T_B S - \alpha p_c ((V_{S_1} + \Delta V_S)(T_{S_1} + \Delta T_S) - V_{S_1} T_{S_1})S - K_c \Delta T_S/(3d)$$

$$= \alpha p_c \Delta V_S T_B S - \alpha p_c \Delta V_{S_1} T_{S_1} S - \alpha p_c V_{S_1} \Delta T_S S - \alpha p_c \Delta V_S \Delta T_S S - K_c \Delta T_S/(3d)$$

$$= \alpha p_c \Delta V_S(T_B - T_{S_1})S - \alpha p_c V_{S_1} \Delta T_S S - \alpha p_c \Delta V_S \Delta T_S S - K_c \Delta T_S/(3d)$$

where
$\alpha$=0.8 (countercurrent heat exchange in a warm condition);
$P_c$=0.92 cal/mL/K (heat capacity of blood);
$V_{s_i}$; i=1,2=the skin blood flow rate at times $t_1$ and $t_2$;
$T_B$=310 K (blood temperature in the core);
$T_{s_i}$; i=1,2=the skin temperature at times $t_1$ and $t_2$;
S=the thickness of the skin;
$K_c$=0.168 kcal/m/h/K (thermal conductivity of skin); and
d=the depth of core temperature point from skin surface.

After differentiating, the following equation is obtained:

$$C_s \frac{dT_S}{dt} \approx \alpha p_c \frac{dV_S}{dt}(T_B - T_S)S - \alpha p_c V_S \frac{dT_S}{dt} S - \alpha p_c \frac{dV_S}{dt} \frac{dT_S}{dt} S - K_c \frac{dT_S}{dt}/(3d).$$

Ignoring the term involving $$\frac{dV_S}{dt}\frac{dT_S}{dt},$$

one obtains the following equation:

$$\frac{dV_S}{dt} = \frac{T_B(C_S + K_c/(3d)) - C}{(T_B - T_S)^2} \frac{dT_S}{dt},$$

where C is a constant.

For calibrated thermal imagery, one can calculate the discrete-time approximation to the derivative of the temperature $$\frac{dT_S}{dt}$$

as the difference between a pair of images normalized by the number of sample frames between the respective acquisition times. The expression $$T_B(C_S + K_c/(3d)) - C$$

represents a constant. Therefore, one can estimate the term $$\frac{dV_S}{dt},$$

except for an unknown scale factor. The expression for $$\frac{dV_S}{dt}$$

can be integrated numerically to obtain an estimate for $V_s$.
To arrive at $$\frac{dV_S}{dt} = \frac{T_B(C_S + K_c/(3d)) - C}{(T_B - T_S)^2} \frac{dT_S}{dt},$$

one must consider the metabolic heat component as negligible.

By solving this equation for every pixel in the image, the raw thermal data can be transformed to blood flow rate data. To ensure a meaningful application of the equation, the image can be cropped so that it contains only the subject's face and no background, e.g., by segmentation, partitioning, etc. For example, cropping can be performed at the first frame of each video clip and cropping dimensions applied across the timeline to the end of a particular question-answer session. This assumes a stationary subject for the short duration (5–10 seconds) of the question-answer session. Based on experimental experience, the stationary subject assumption is valid, although some agitated subjects moving noticeably during such short periods of time may affect some determinations.

Figure 16:
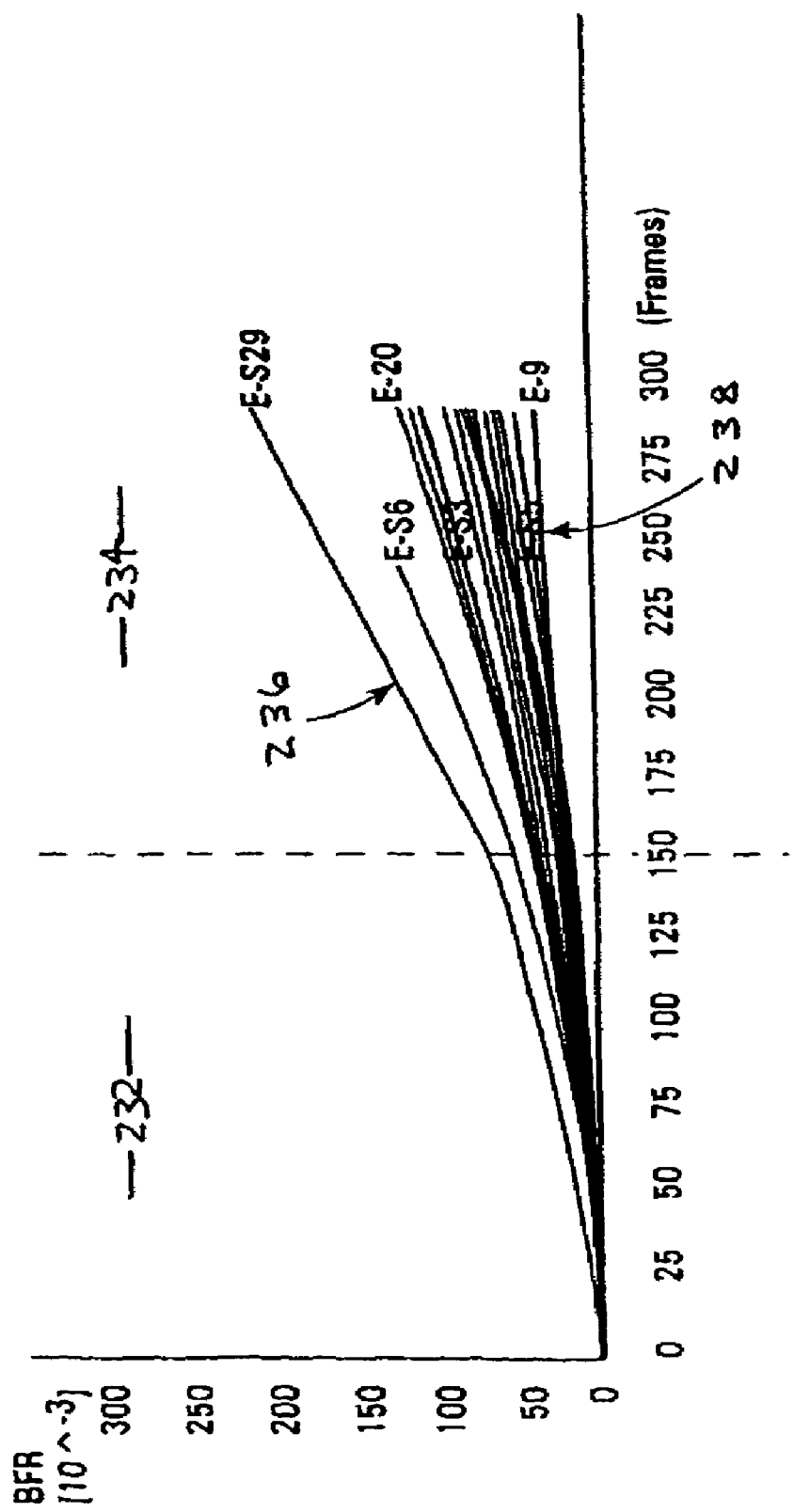
FIG. 16 is a graph for use in describing an illustrative example of a thermal image data analysis process such as that shown generally in FIG. 3 according to the present invention.

In the embodiment of FIG. 14, the respective average blood flow rate for each frame is then determined and a signal is produced representative of average blood flow rate from frame to frame. Such a signal for which an example has been plotted in FIG. 16, provides blood flow rate over frames of thermal image data that can be used for classification purposes.

After transformation of the thermal image data to blood flow rate data (block 204), as shown in FIG. 14, such change of blood flow rate over time may be used to classify a person's response to the question as deceptive or non-deceptive based on the change of blood flow rate over time (block 206).

Classifying the person's response to the question as deceptive or non-deceptive based on the change of blood flow rate (block 206) may be performed via one or more different classification processes. Two specific classification processes are described with reference to FIGS. 15A–15B, wherein a slope threshold is generated. However, various other classification processes are possible.

For example, software associated with computer apparatus 60 may allow for the direct display or visualization of blood flow rate data in terms of the intensity of such blood flow rate data. For example, such data may be provided in grayscale values even though such grayscale display of images may generally have a poor visualization effect. Other commonly employed rainbow pseudo-color display schemes may provide relatively better visualization effects.

In other words, blood flow rate data may be directly displayed on a display screen and classification may be performed manually by the person viewing the blood flow rate data on the display. For example, as shown in FIGS. 10A–10B, a large difference in blood flow rate data is visually displayed. The user may manually classify the individual as being deceptive or non-deceptive based on the change of blood flow rate data viewed on the display. As such, classification software component (block 206) may be implemented through software that displays the blood flow rate data of the human face or a region thereof to a user, e.g., using a rainbow pseudo-coloring technique. However, preferably, other types of classification processes, e.g., automated, real-time systems, are preferred.

For example, pattern recognition/classification software may perform automatic classification. Preferably, such algorithms of the software operate in a training and performance mode. For example, in the training mode, the software component may include algorithms that belong to the class of statistical learning methodology such as described in M. I. Jordan and R. A. Jacobs, entitled "Hierarchical Mixtures of Experts and the EM Algorithm," Neural Computation, Vol. 6, pps. 181–214 (1994). In such a training mode, as the routine learns about the statistical blood flow rate data with regard to individuals in deceptive versus non-deceptive states, algorithms can be updated and the accuracy of such classifications will become more reliable. The performance mode of the algorithm operates to perform the actual classification.

Further, the classification process may use a comparison of blood flow rate data to a determined baseline to perform classification. The baseline reference may, for example, be a baseline of a deceptive versus a non-deceptive blood flow rate or signature of a deceptive person. For example, statistical analysis may be used to develop a baseline for an individual in a non-deceptive state versus a deceptive state. Various response variabilities across the human race may need to be considered.

In other words, the dependence of the non-deceptive state versus deceptive state may be shown by varied blood flow rate images depending on various factors. For example, the mental state of the individual, the intelligence of the individual, the race of an individual, the physical conditioning of an individual, the blood pressure of an individual, and many other variables across the human population will effect the blood flow rate data of an individual in a deceptive versus a non-deceptive situation.

In addition, other conditions relative to obtaining thermal image data from an individual must also be considered. For example, the effect of temperature and light on the scene may need to be considered.

As such, with a collection of experimental data and analysis thereof, a baseline reference covering a large population may be determined.

Once a baseline reference is set, e.g., such as for a particular region (e.g., periorbital region) of the face, then thermal image data may be acquired, transformed to blood flow rate data, and compared to the baseline reference. For example, thermal image data may be captured and transformed for a periorbital region of an individual. Thereafter, the blood flow rate data for the periorbital region can be compared to a threshold level determined from the baseline reference developed for an individual in a deceptive versus non-deceptive state.

Yet further, the blood flow rate data, or signals representative thereof, may be used as feature vectors in a nearest neighbor (NN) classifier setting such as that described in E. Gose et al., entitled, "Pattern Recognition and Image Analysis," pp. 159–186, Prentice-Hall, Upper Saddle River, N.J. (1993). Nearest in NN refers to the smallest Euclidean distance in 300-dimensional space, where 300 is the number of frames acquired. In such a process, the aim is to classify the majority of the subjects based on their distance from a small number of control subjects. The population of the control subjects should be unbiased.

Alternatively, one can establish the ideal blood flow rate signals for the deceptive and non-deceptive case and measure the respective Euclidean distances. These ideal deceptive and non-deceptive blood flow rate signals should correspond to the expected physiological response in stressful and non-stressful situations.

Figure 15A:
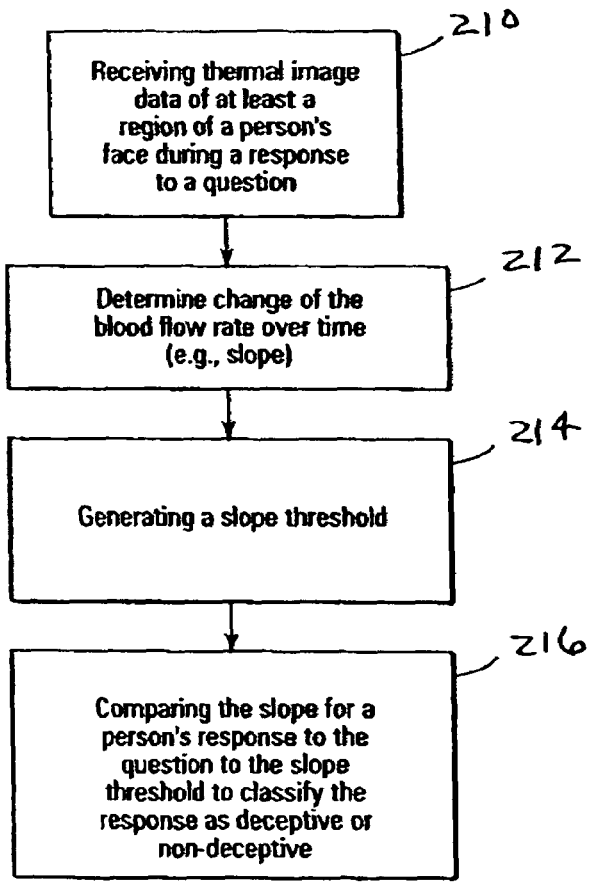
FIGS. 15A–15B show alternative flow diagrams of the transformation and classification processes shown generally in the thermal image data analysis process shown generally in FIG. 8 according to the present invention.

FIG. 15A shows one embodiment of a classification process based on a slope threshold generated using a thresholding algorithm applied to slope data of deceptive and non-deceptive change in blood flow rate over time. As shown in FIG. 15A, thermal image data is received for at least a region of a person's face during a response to a question (block 210). Thereafter, change of the blood flow rate over time is determined (block 212).

The slope threshold generated is based on slope data for a number of subjects, both non-deceptive and deceptive (block 214). Ideally, the slope data should form a bi-modal distribution; one for the non-deceptive subjects and one for the deceptive subjects. This classifier can be tested by feeding the slope data into a thresholding algorithm. For example, the slope data may be representative of the change of blood flow rate over time during responses of subjects (see, for example, region 234 in FIG. 16.)

One such thresholding algorithm that may be used is described in the article by N. Otsu, entitled "A Threshold Selection Method from Gray-Level Histograms," *IEEE Transactions on Systems, Man & Cybernetics*, Vol. 9, No. 1, pps. 62–65 (1979). This algorithm has reliable performance in bi-modal distributions. It involves a non-parametric and unsupervised method of threshold selection. An optimal threshold is selected in order to maximize the separability of the result in classes. The algorithm utilizes only the zeroth-order and first-order cumulative moments of the histogram.

Once the slope threshold is generated based on the slope data for a plurality of non-deceptive and deceptive subjects, then the slope threshold can be used to make binary decisions. Such binary decisions can be made by comparing the slope representative of the change of blood flow rate over time for a person responding to a question to the slope threshold so as to classify the person's response as deceptive or non-deceptive (block 216). For example, if the slope is smaller than the threshold, then one may classify the answer as a non-deceptive response, e.g., the subject being non-deceptive. Likewise, if the slope is larger than the slope threshold, then one can classify the elicited response or answer as deceptive.

Figure 15B:
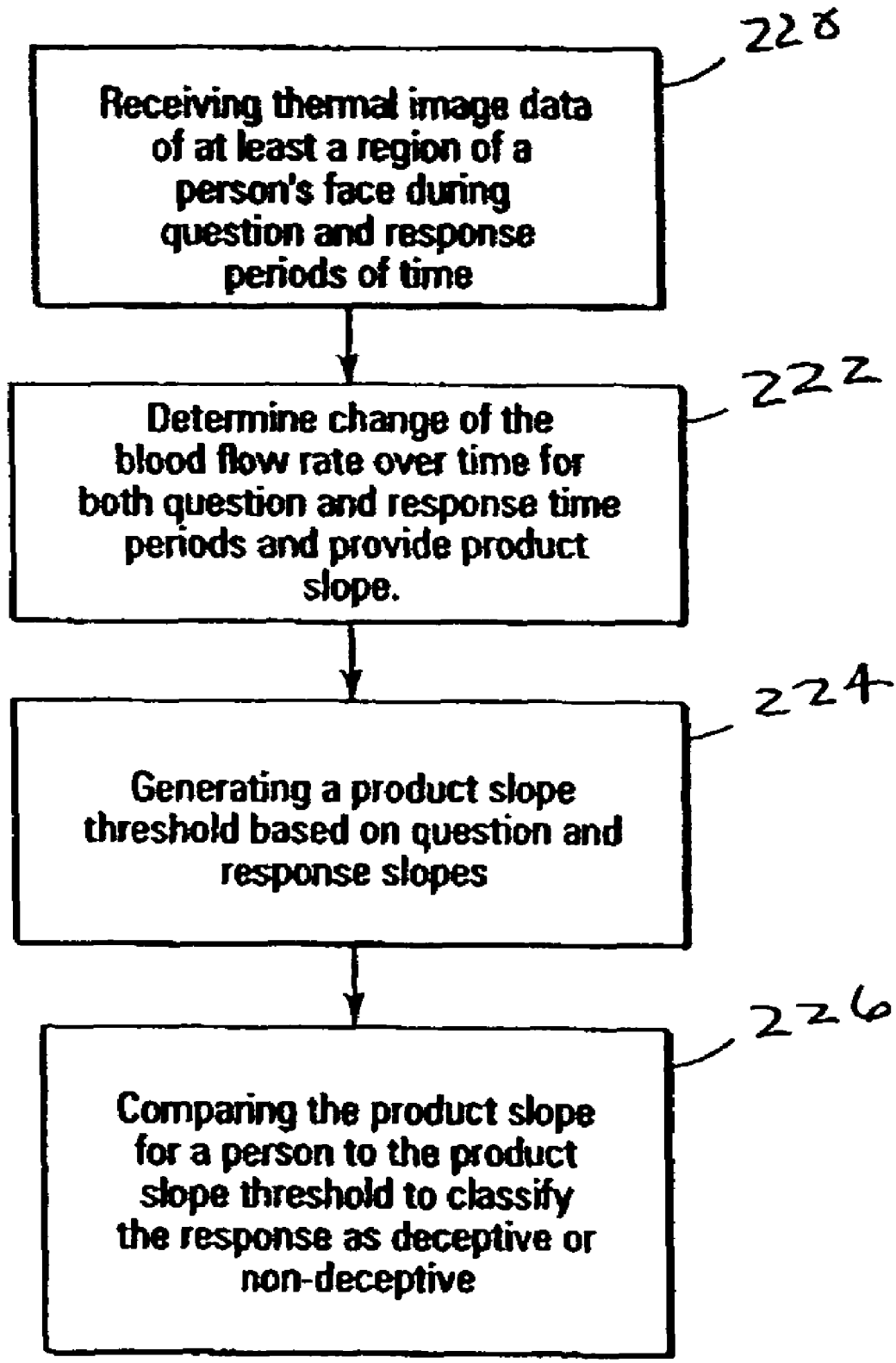

FIG. 15B shows a classification process that is substantially the same as the classification process described with reference to FIG. 15A, except that the slope threshold generated is a product slope threshold based on the product of the slope representative of the change of blood flow rate over time for a plurality of deceptive and non-deceptive persons during the question time period (see, for example, region 232 of FIG. 16) and the slope representative of the change of blood flow rate over time for a plurality of deceptive and non-deceptive persons during the response time period (see, for example, region 234 of FIG. 16). In other words, as shown in FIG. 15B, thermal image data is received for at least a region of a person's face during a question period of time and a time period during a response to the question (block 220). The thermal image data is transformed to determine the change of blood flow rate over time as shown in block 222 for the person during both such periods of time to provide a product slope of the question and answer time periods.

A product slope threshold is generated (block 224). The product slope threshold is generated using the slope representative of the change of the blood flow rate over time for a plurality of subjects, both non-deceptive and deceptive, during both the question period of time and the response period of time. In other words, as described above, the slope representative of the change of blood flow rate over time for each person during the question time period is multiplied times the slope representative of the change of blood flow rate over time for the person during the response time period to obtain a product slope. A thresholding algorithm such as that described above is applied to the product slopes to obtain the product slope threshold.

Thereafter, a binary decision is made with regard to the response to the question and the elicited response is determined as being deceptive or non-deceptive based on the product slope threshold (block 226). In other words, the product slope for a person is compared to the product slope threshold to classify a response from the person as deceptive or non-deceptive.

Although various exemplary processes have been provided as illustrative embodiments for classifying an individual as providing a deceptive or non-deceptive response to a question, one skilled in the art will readily recognize that other classification processes using blood flow rate data obtained from thermal image data of the human face 130 may be used according to the present invention.

All references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. A method for use in detecting a physiological state of a person, the method comprising:
   providing an enclosure, wherein the enclosure comprises a first enclosed volume and a second enclosed volume physically separated from the first enclosed volume, wherein the enclosure further comprises an entrance door sized to allow a person to enter the first enclosed volume;
   controlling one or more characteristics of the environment within the first enclosed volume;
   permitting only a single person to enter the first enclosed volume through the entrance door;
   asking the person within the first enclosed volume one or more questions so as to elicit a response from the person;
   providing thermal infrared image data of at least a region of the face of the person during at least a portion of the response from the person using at least one thermal infrared imaging device, wherein the at least one thermal infrared imaging device is positioned within the second enclosed volume; and
   using the thermal infrared image data to determine a physiological state of a person.

2. The method of claim 1, wherein the enclosure further comprises an exit door sized to allow a person to exit the first enclosed volume, wherein the entrance door and the exit door provide different openings of the enclosure, and further wherein the method comprises permitting the person within the first enclosed volume to exit the enclosure via the exit door.

3. The method of claim 1, wherein the enclosure is one of a plurality of enclosures positioned side by side.

4. The method of claim 3, wherein the enclosures are portable, and further wherein the method comprises moving one or more of the enclosures from a first location to a second location.

5. The method of claim 1, wherein the method further comprises allowing the person to be seated at a position within the first enclosed volume.

6. The method of claim 1, wherein controlling one or more of the characteristics of the environment within the first enclosed volume comprises controlling at least one characteristic selected from a group consisting of temperature, light intensity, air movement, and noise.

7. The method of claim 1, wherein controlling one or more of the characteristics of the environment within the first enclosed volume comprises:
   sensing one or more environmental parameters within the first enclosed volume; and
   controlling one or more of the characteristics of the environment within the first enclosed volume based thereon.

8. The method of claim 1, wherein asking the person within the enclosure one or more questions so as to elicit a response from the person comprises:
   prerecording the one or more questions; and
   presenting the one or more prerecorded questions to the person.

9. The method of claim 8, wherein presenting the one or more prerecorded questions to the person comprises displaying an animated or a video recorded figure presenting the one or more prerecorded questions to the person.

10. The method of claim 8, wherein presenting the one or more prerecorded questions to the person comprises:
    detecting one or more responses from the person; and
    synchronizing the presentation of the one or more prerecorded questions with the one or more detected responses from the person.

11. The method of claim 1, wherein permitting a person to enter the first enclosed volume through the entrance door comprises authorizing the person to enter the first enclosed volume, wherein such authorization permits the entrance door to be unlocked.

12. The method of claim 1, wherein providing thermal infrared image data of at least a region of the face of the person comprises:
focusing a thermal infrared image device operable to provide thermal image data on at least the region of the face of the person; and
capturing thermal image data from at least a region of the face of the person during at least a portion of the response from the person.

13. The method of claim 1, wherein using the thermal image data to determine a physiological state of a person comprises using the thermal infrared image data to determine anxiety in the person.

14. The method of claim 1, where using the thermal image data to determine a physiological state of a person comprises using the thermal infrared image data to determine whether the person is deceptive or non-deceptive.

15. The method of claim 14, wherein using the thermal infrared image data to determine whether the person is deceptive or non-deceptive comprises:
providing the thermal image data from at least a region of the face of the person; and
transforming the thermal image data to blood flow rate data for use in determining whether the person is deceptive or non-deceptive.

16. The method of claim 15, wherein determining whether the person is deceptive or non-deceptive comprises classifying the person as deceptive or non-deceptive based on a change of blood flow rate over time in the at least one region of the face.

17. The method of claim 15, wherein transforming the thermal image data comprises transforming the thermal image data using a blood flow rate model where blood flow rate is inversely proportional to the square of skin temperature deviation from a core temperature of a human body.

18. The method of claim 1, wherein the method further comprises providing measurement of one or more physiological parameters in addition to the thermal image data, and further wherein using the thermal infrared image data to determine a physiological state of a person comprises using the thermal infrared image data and the one or more physiological parameters to determine a physiological state of a person.

19. The method of claim 1, wherein providing thermal infrared image data comprises providing the thermal image data to a computing apparatus, wherein the computing apparatus is positioned within the second enclosed volume.

20. A system for use in detecting a physiological state of a person, the system comprising:
an enclosure sized to accommodate only a single person therein, wherein the enclosure comprises a first enclosed volume and a second enclosed volume physically separated from the first enclosed volume, wherein the enclosure comprises an entrance door sized to allow a person to enter the first enclosed volume;
one or more environment control devices for use in controlling one or more characteristics of the environment within the first enclosed volume;
a display apparatus and a speaker apparatus operable to present one or more prerecorded questions to a person occupying the first enclosed volume so as to elicit one or more responses therefrom;
a thermal infrared imaging device positioned within the second enclosed volume operable to provide thermal infrared image data of at least a region of the face of a person when the first enclosed volume is occupied by the person; and
a computing apparatus operable upon the thermal infrared image data to determine a physiological state of the person occupying the first enclosed volume.

21. The system of claim 20, wherein the enclosure further comprises an exit door sized to allow a person to exit the first enclosed volume, wherein the entrance door and the exit door are different openings of the enclosure.

22. The system of claim 20, wherein the enclosure is one of a plurality of enclosures positioned side by side.

23. The system of claim 22, wherein one or more of the plurality of enclosures is portable and movable from a first location to a second location.

24. The system of claim 23, wherein one or more of the enclosures comprises a set of transfer wheels on a lower surface thereof.

25. The system of claim 20, wherein the system further comprises a seat positioned within the first enclosed volume to allow a person to be seated at a position therein.

26. The system of claim 20, wherein the one or more environment control devices comprise an air modification apparatus operable to adjust temperature within the first enclosed volume, wherein the system further comprises at least one temperature sensor located within the first enclosed volume to sense the temperature within the first enclosed volume, and wherein the temperature within the first enclosed volume is controlled as a function of the sensed temperature.

27. The system of claim 20, wherein the one or more environment control devices comprise a light source operable to adjust light intensity within the first enclosed volume, wherein the system further comprises at least one light sensor located within the first enclosed volume to sense light intensity within the first enclosed volume, and wherein the light intensity within the first enclosed volume is controlled as a function of the sensed light intensity.

28. The system of claim 20, wherein the one or more environment control devices comprise an air modification apparatus operable to adjust air flow within the first enclosed volume, wherein the system further comprises at least one air flow sensor located within the first enclosed volume to sense air movement within the first enclosed volume, and wherein the air flow within the first enclosed volume is controlled as a function of the sensed air movement.

29. The system of claim 20, wherein the display apparatus and the speaker apparatus are operable under control of the computing apparatus to provide an animated or a video recorded figure presenting one or more prerecorded questions to the person.

30. The system of claim 20, wherein the system further comprises a microphone located in the first enclosed volume for use in detecting one or more responses from the person in the first enclosed volume, and wherein the display apparatus and the speaker apparatus are operable under control of the computing apparatus to synchronize the one or more prerecorded questions with the one or more detected responses from the person.

31. The system of claim 20, wherein the system further comprises an identification authorization apparatus associated with the entrance door to provide authorization to a person waiting to enter the first enclosed volume, wherein the entrance door is unlocked only upon a person receiving such authorization.

32. The system of claim 20, wherein the computing apparatus is operable to determine anxiety in the person based on thermal infrared image data.

33. The system of claim 20, where the computing apparatus is operable to determine whether a person in the first enclosed volume is deceptive or non-deceptive using the thermal infrared image data.

34. The system of claim 33, wherein the computing apparatus is further operable to transform the thermal infrared image data to blood flow rate data for use in determining whether the person is deceptive or non-deceptive.

35. The system of claim 33, wherein the computing apparatus is further operable to classify the person as deceptive or non-deceptive based on a change of blood flow rate over time in the at least one region of the face.

36. The system of claim 35, wherein the computing apparatus is further operable to transform the thermal infrared image data using a blood flow rate model where blood flow rate is inversely proportional to the square of skin temperature deviation from a core temperature of a human body.

37. The system of claim 33, wherein the thermal infrared image device is operable to capture thermal image data during at least a period of time during at least an elicited response from a person in the first enclosed volume.

38. The system of claim 20, wherein the system further comprises means for providing measurement of one or more physiological parameters in addition capturing the thermal infrared image data, and further wherein the computing apparatus is operable to determine whether the person is deceptive or non-deceptive using the thermal infrared image data and the one or more physiological parameters.

39. The system of claim 20, wherein the computing apparatus is positioned in the second enclosed volume.

* * * * *